United States Patent
Azar et al.

(10) Patent No.: US 11,844,958 B2
(45) Date of Patent: Dec. 19, 2023

(54) GLAND TREATMENT DEVICES AND METHODS FOR TREATING DRY EYE DISEASE

(71) Applicant: Twenty Twenty Therapeutics LLC, South San Francisco, CA (US)

(72) Inventors: Dimitri Azar, San Francisco, CA (US); Timothy Stowe, Alameda, CA (US)

(73) Assignee: TWENTY TWENTY THERAPEUTICS LLC, South San Francisco, CA (US)

( * ) Notice: Subject to any disclaimer, the term of this patent is extended or adjusted under 35 U.S.C. 154(b) by 196 days.

(21) Appl. No.: 15/931,563

(22) Filed: May 13, 2020

(65) Prior Publication Data

US 2020/0360723 A1 Nov. 19, 2020

Related U.S. Application Data

(60) Provisional application No. 62/847,576, filed on May 14, 2019.

(51) Int. Cl.
*A61N 5/06* (2006.01)
*A61N 5/00* (2006.01)
*A61H 23/02* (2006.01)

(52) U.S. Cl.
CPC ........... *A61N 5/0625* (2013.01); *A61H 23/02* (2013.01); *A61H 2201/0207* (2013.01);
(Continued)

(58) Field of Classification Search
CPC .......... A61N 5/0625; A61N 2005/0626; A61N 2005/0635; A61N 2005/0652;
(Continued)

(56) References Cited

U.S. PATENT DOCUMENTS

| 4,198,714 A * | 4/1980 | Jensen ...................... A61F 2/16 623/6.51 |
| 8,255,039 B2 | 8/2012 | Gravely et al. |

(Continued)

FOREIGN PATENT DOCUMENTS

| JP | 2000139998 A | 5/2000 |
| JP | 2016522711 A | 8/2016 |

(Continued)

OTHER PUBLICATIONS

Study: Scleral Lenses Coated with Tangible Hydra-PEG Improve Dry Eye Symptoms, Comfort (Tangible Science) Jan. 29, 2019 (Jan. 29, 2019) Retrieved from the Internet on Sep. 9, 2020. URL: <https://eyewire.news/ articles/controlled-trial-shows-promise-of-donated-stem-cells-in-restoring-vision/>.

(Continued)

*Primary Examiner* — Carl H Layno
*Assistant Examiner* — Aya Ziad Bakkar
(74) *Attorney, Agent, or Firm* — TAROLLI, SUNDHEIM, COVELL & TUMMINO L.L.P.

(57) ABSTRACT

Systems, devices and methods that facilitate safe heating of eyelids to treat dry eye are disclosed. According to one embodiment, an apparatus for optical heating of an eyelid of a patient includes: a housing configured to be grasped by a human hand; at least one light emitter coupled to the housing and configured to emit beams of infrared light; a waveguide component coupled to the at least one light emitter and configured to direct the beams of light toward the eyelid; and a scleral cover configured to couple to the housing, the scleral cover comprising: a curved protective portion configured to reflect infrared light emanating from the at least one light emitter.

13 Claims, 16 Drawing Sheets

(52) U.S. Cl.
CPC .............. *A61H 2201/1418* (2013.01); *A61H 2201/5082* (2013.01); *A61N 2005/005* (2013.01); *A61N 2005/0626* (2013.01); *A61N 2005/0635* (2013.01); *A61N 2005/0652* (2013.01); *A61N 2005/0659* (2013.01); *A61N 2005/0666* (2013.01)

(58) Field of Classification Search
CPC .... A61N 2005/0659; A61N 2005/0666; A61N 2005/0648; A61H 23/02; A61H 2201/0207; A61H 2201/1418; A61H 2201/5082
See application file for complete search history.

(56) References Cited

U.S. PATENT DOCUMENTS

| | | | |
|---|---|---|---|
| 8,491,508 | B2 | 7/2013 | Smith et al. |
| 9,510,972 | B2 | 12/2016 | Badawi |
| 10,130,507 | B2 | 11/2018 | Whitehurst et al. |
| 2007/0191821 | A1 | 8/2007 | Boxer Wachler |
| 2012/0088980 | A1 | 4/2012 | Gravely et al. |
| 2014/0192327 | A1 | 7/2014 | Sindt et al. |
| 2014/0330129 | A1 | 11/2014 | Grenon et al. |
| 2015/0057701 | A1* | 2/2015 | Kelleher ............ A61H 23/0245 606/204.15 |
| 2016/0258964 | A1* | 9/2016 | Zhang .................... G01N 33/66 |
| 2018/0001108 | A1 | 1/2018 | Kelleher |
| 2018/0064962 | A1 | 3/2018 | Bujak et al. |
| 2019/0091065 | A1 | 3/2019 | Kelleher et al. |

FOREIGN PATENT DOCUMENTS

| | | | |
|---|---|---|---|
| JP | 2017533074 A | 11/2017 | |
| WO | 2018098419 A1 | 5/2018 | |
| WO | WO-2018098419 A1 * | 5/2018 | .............. A61N 1/00 |
| WO | 2018153368 A1 | 8/2018 | |
| WO | 2019033415 A1 | 2/2019 | |
| WO | WO-2019033415 A1 * | 2/2019 | ......... B29C 33/3842 |

OTHER PUBLICATIONS

International Search Report and Written Opinion for PCT/US20/32829, dated Oct. 6, 2020, 16 pages.
Mechanical characterization of bulk Sylgard 184 for microfluids and microengineering (Johnston D. et al.) Feb. 28, 2014. Retrieved from the Internet on Sep. 9, 2020. URL: <https://iopscience.iop.org/article/10.1088/0960-1317/24/3/03501/meta>.
Office Action from the Japanese Patent Office for Corresponding Application Serial No. 2021-568141, pp. 1-4.
European Office Action for Corresponding Application Serial No. 20806379.2, dated Jan. 5, 2023, pp. 1-7.

* cited by examiner

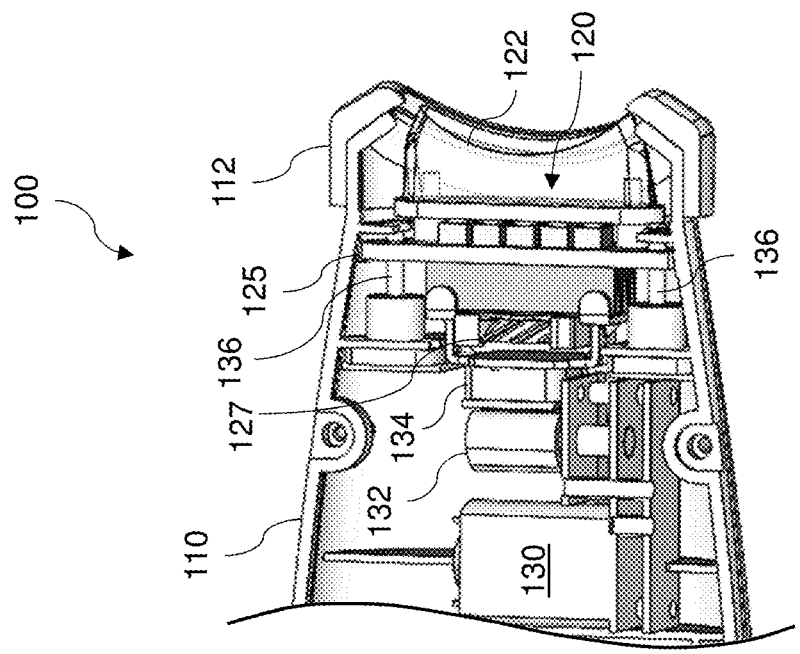
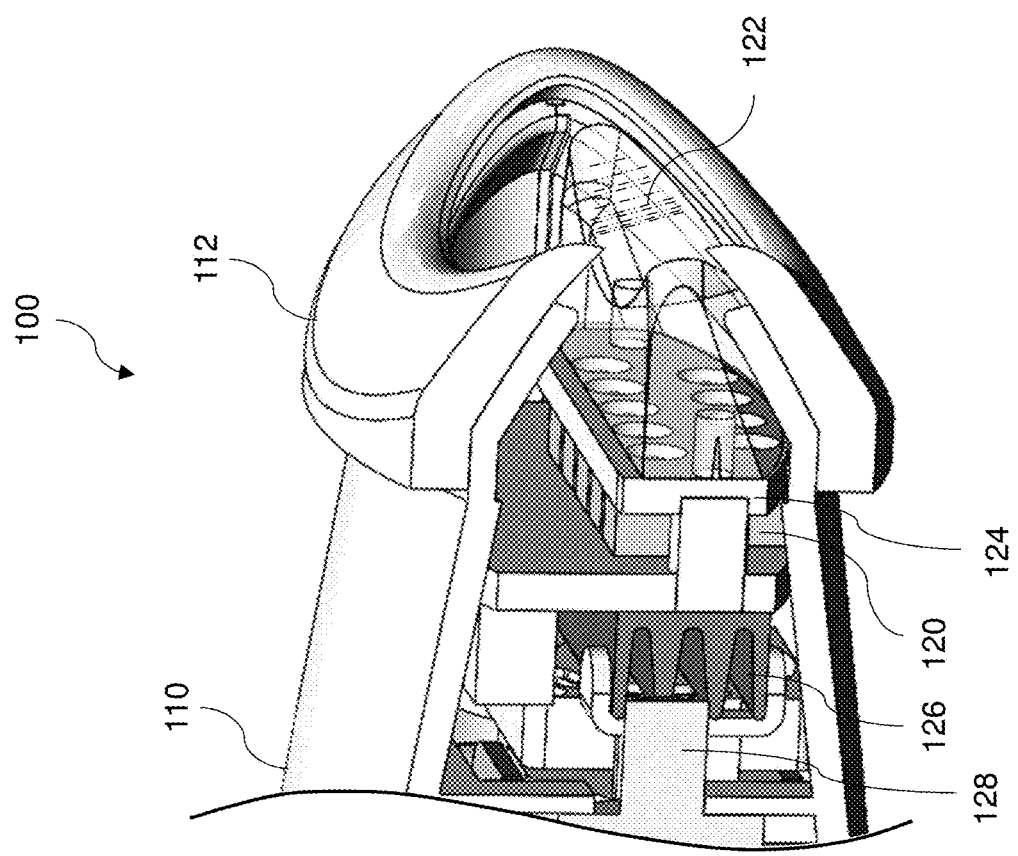
Fig. 2B
Fig. 2A

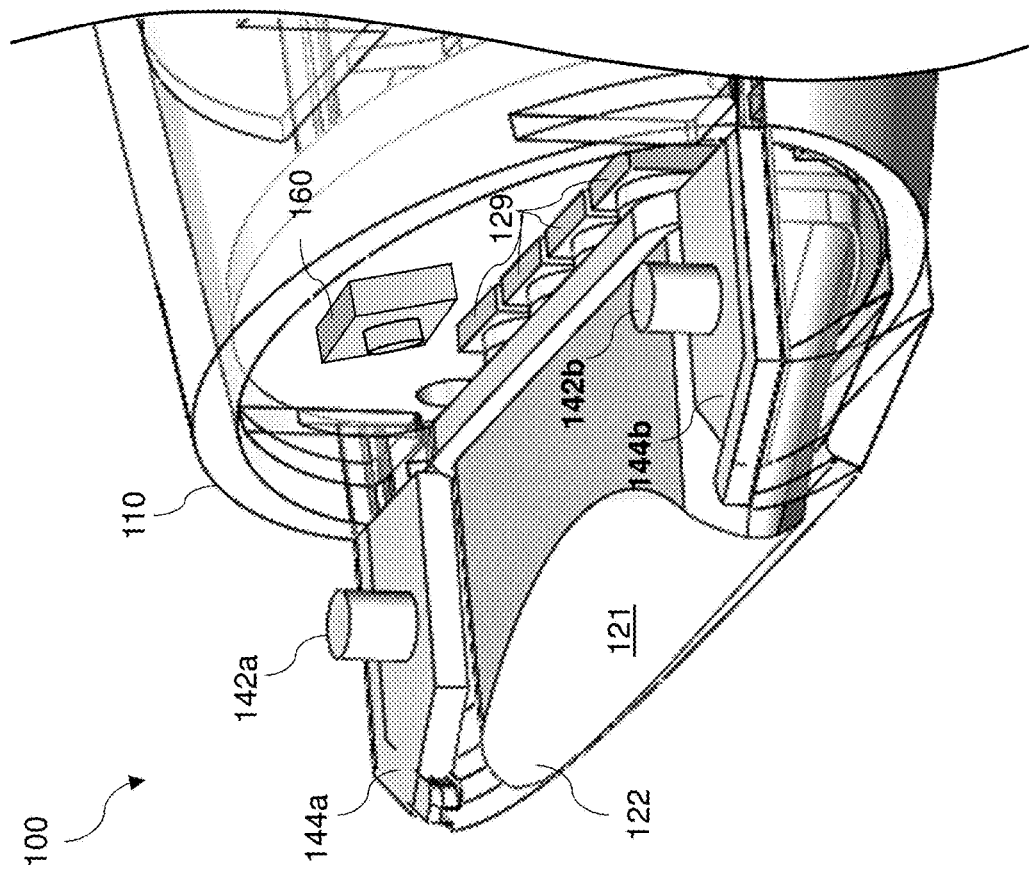

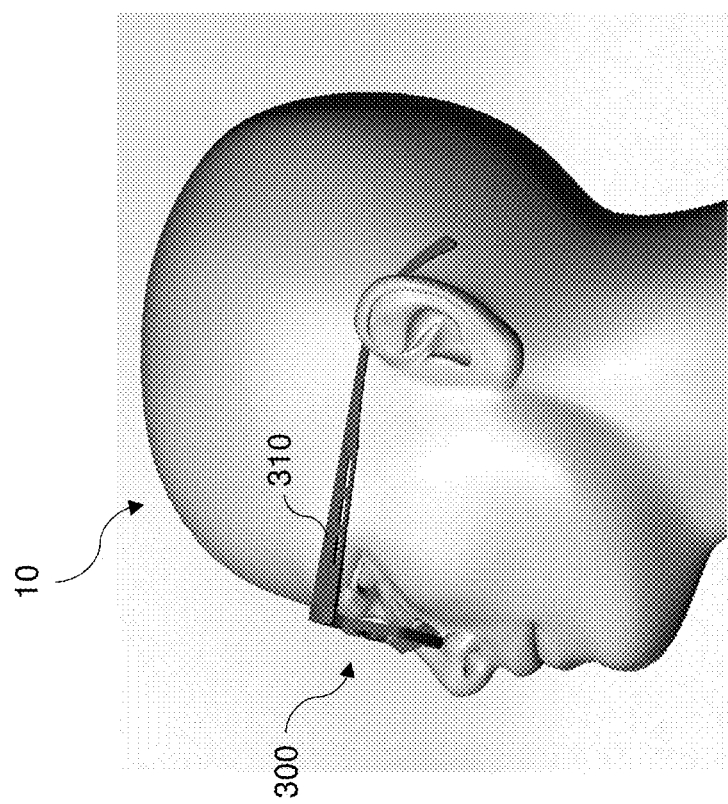

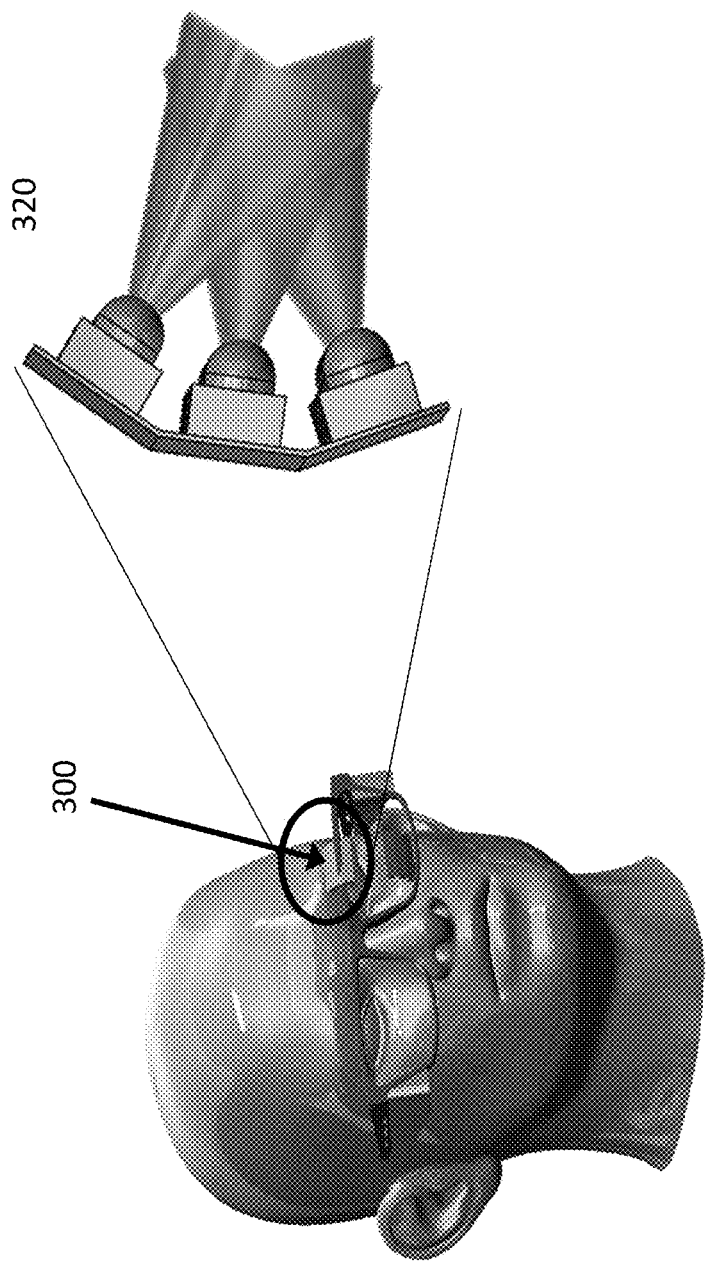

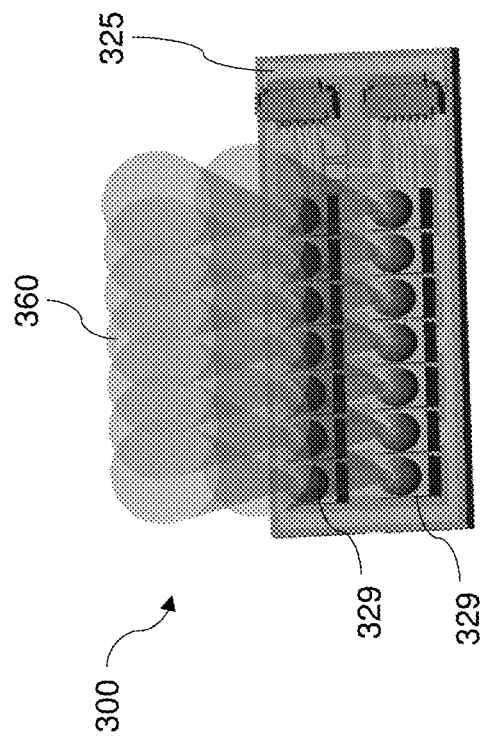
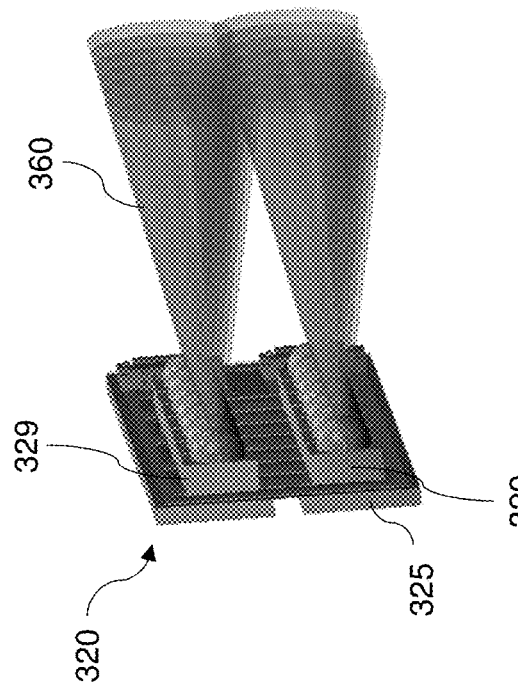
Fig. 20A
Fig. 20B

GLAND TREATMENT DEVICES AND METHODS FOR TREATING DRY EYE DISEASE

CROSS-REFERENCES TO RELATED APPLICATIONS

The present application claims the benefit of and priority to U.S. Provisional Patent Application No. 62/847,576, filed May 14, 2019, the entirety of which is hereby incorporated by reference.

TECHNICAL FIELD

The present disclosure relates generally to ophthalmic devices and associated methods for treating dry eye, and, in particular but not exclusively, relates to ophthalmic devices for treating dry eye disease by safely heating Meibomian glands.

BACKGROUND

Dry eye disease, or DED, affects millions of people worldwide. According to some studies, the third most common reason for visiting an ophthalmologist's office is for dry eye disease symptoms. Recently it has been shown that up to 80% of dry eye cases also have a component called Meibomian gland dysfunction or MGD. Normally, the lipid layer produced by the Meibomian (also expressed as Meibomian) glands spreads evenly into a thin (thickness in nanometers) protective film over the air-tear interface above the cornea. Every time a person blinks a slight amount of lipid protective film is spread. However, there are many conditions under which this oily layer no longer spreads out evenly over the tear film and this process can be interrupted, reduced, or even stopped entirely. These root causes can include but are not limited to hormonal changes in the oil production properties with age, skin mites living in the eyelashes, prolonged infection such as difficult to remove styes, general inflammation (Blepharitis), autoimmune diseases or allergic reactions, and more recently the inadequate blinking from excessive screen time known as computer vision syndrome. (CVS).

The absence of an outer protective lipid layer reduces the evaporation time for the tear film covering the eye, leading to the possibility of dry spots over the cornea epithelium. This is measured quantitatively as the so-called tear film break-up time metric abbreviated as TBUT or TFBUT.

In the past, mild MGD has been addressed by using warm compresses, eyelid cleansing compounds, and massaging the eyelids gently. However, these approaches have not been shown to clinically be effective in the majority of severe dry eye cases.

More recent treatments have been used which include heating up the Meibomian glands from inside the eyelids to melt or soften the oils which have become clogged. As the eyelids are heated from the inside, heat is delivered directly to the Meibomian gland. In some instances, air bladders are also used to massage the Meibomian glands to help express the softening oil clogs from the glands. However, such procedures can still be highly invasive and costly procedures requiring an expert ophthalmologist, anesthesia, and multiple treatments each year. Other known eye treatments include heating the outside of the eyelids using heating pads. In this type of procedure, ophthalmologists must still use forceps with an intermediate pressure to effectively express the glands. Such treatments are also invasive and can be uncomfortable for the patient.

SUMMARY

Aspects of the present disclosure include a light-based gland treatment device that directs electromagnetic radiation (e.g., infrared light) to the gland through an elastomeric optical waveguide. Additionally, a therapeutic device may include a mechanical oscillator assembly that periodically compresses and massages the tissue around the gland to remove clogged oils from the gland. In one embodiment, a gland treatment device includes an infrared (IR) light element positioned within a housing and configured to emit light through a distal opening. An elastomeric waveguide is coupled to, or positioned in front of, the light element and is sized, shaped, and structurally arranged to guide or direct the light through a distal surface of the waveguide. The distal surface of the waveguide may be concave to conform to the curvature of the patient's eyelid. The device may include a massaging assembly configured to oscillate the waveguide and light element along a longitudinal axis. A scleral cover or eye shield sits underneath the eyelids and comprises a tab or bracket mechanically coupled or attached to the housing such that the massaging assembly moves the elastomeric waveguide longitudinally relative to the cover. Accordingly, when the scleral cover is positioned over the cornea and attached to the housing, the massaging assembly compresses the eyelid between the scleral cover and the elastomeric waveguide. Thus, the force applied by the massaging component can be focused on the eyelid and Meibomian gland rather than into the patient's eyeball.

According to one embodiment, an apparatus for optical heating of an eyelid of a patient includes: a housing configured to be grasped by a human hand; at least one light emitter coupled to the housing and configured to emit beams of infrared light; a waveguide component coupled to the at least one light emitter and configured to direct the beams of infrared light toward the eyelid; and a scleral cover configured to couple to the housing. In some embodiments, the scleral cover includes: a curved protective portion configured to reflect infrared light emanating from the at least one light emitter.

In some embodiments, the scleral cover includes a biocompatible acrylic material and a titanium dioxide additive incorporated within the biocompatible acrylic material. In some embodiments, an outer surface of the scleral cover comprises a dielectric coating that is more transmissive in visible light wavelengths than in infrared wavelengths. In some embodiments, an inner surface of the scleral cover comprises a Hydra-PEG coating. In some embodiments, the scleral cover comprises a tab configured to engage a mechanical coupling feature of the housing. In some embodiments, the apparatus further includes an imaging component coupled to the housing. In some embodiments, the scleral cover further comprises a viewing window comprising a transparent body coupled to the tab, the transparent body comprising an angled viewing surface forming an oblique angle with the tab. In some embodiments, the imaging component is oriented to obtain images of the eyelid of the patient through the viewing window.

In some embodiments, the waveguide component comprises a low durometer material and is at least partially transparent for the infrared light emitted by the light emitter. In some embodiments, the apparatus further includes an actuator coupled to the waveguide component and configured to cause the waveguide component to move in a longitudinally oscillating manner. In some embodiments, the scleral cover comprises at least one of a temperature sensor circuit or a device identification circuit. In some embodiments, the at least one of the temperature sensor circuit or the device identification circuit comprises a radiofrequency identification (RFID) circuit disposed on a surface of the scleral cover. In some embodiments, the apparatus further comprises an RFID transceiver coupled to the housing and configured to: provide power to the RFID circuit of the scleral cover; and receive at least one of a device identification signal or a temperature measurement signal from the RFID circuit of the scleral cover.

According to another embodiment of the present disclosure, a device for treating glands in an eyelid of a patient includes: a housing; a light delivery assembly comprising: one or more light-emitting diodes (LEDs) positioned within the housing, wherein the one or more LEDs are configured to emit light through a distal opening of the housing; a waveguide positioned over the one or more LEDs and positioned within the distal opening of the housing; and an actuator configured to cause the one or more LEDs and the waveguide to oscillate in a longitudinal direction while the one or more LEDs are emitting light through the waveguide. In some embodiments, the actuator comprises an electric motor, and the device further comprises: a cam coupled to the housing and abutting a surface of the light delivery assembly, wherein the electric motor is configured to cause the cam to rotate and periodically cause the light delivery assembly to advance distally and retract proximally relative to the housing. In some embodiments, the one or more LEDs comprise at least one of: one or more short wave infrared (SWIR) LEDs configured to emit light having a spectral range of 1050 nm-1200 nm; or one or more infrared LEDs configured to emit light having a center wavelength of approximately 980 nm and a spectral range between 940-1000 nm. In some embodiments, the waveguide comprises an elastomeric material, and wherein the waveguide is sized and shaped such that internal surfaces of the waveguide are configured to internally reflect diverging portions of the light and direct the reflected light through a distal surface of the waveguide. In some embodiments, the device further includes an imaging component coupled to the housing and configured to obtain images of the eyelid margin of the patient during a treatment procedure.

According to another embodiment of the present disclosure, a protective scleral cover, includes: a curved body sized and shaped to be positioned on a patient's eye, wherein the curved body comprises an inner surface having a concave shape and an opposite outer surface having a convex shape; and a flat tab protruding outward from the outer surface of the curved body and comprising at least one mechanical coupling feature to engage the housing. In some embodiments, the curved body includes a reflective material, where the curved body and the flat tab are integrally formed and comprise a polymer material.

In some embodiments, the protective scleral cover further includes an RFID temperature-sensing circuit integrated within the curved body. In some embodiments, the RFID temperature-sensing circuit comprises a memory component having stored thereon authorization information associated with the protective scleral cover. In some embodiments, the reflective material is incorporated into the polymer material. In some embodiments, the reflective material forms a reflective coating disposed over the outer surface of the curved body.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 2A is a cross-sectional view of a gland treatment device, according to an embodiment of the present disclosure.

FIG. 2B is a cross-sectional view of a gland treatment device, according to an embodiment of the present disclosure.

FIG. 3 is a partially transparent view of a gland treatment device, according to an embodiment of the present disclosure.

FIG. 18 is a perspective view of a wearable gland treatment device mounted on a glasses frame, according to an embodiment of the present disclosure.

FIG. 19A is a perspective view of a wearable gland treatment device mounted on a glasses frame, according to an embodiment of the present disclosure.

FIG. 19B is a perspective view of an IR LED circuit of the wearable gland treatment device shown in FIG. 19A, according to an embodiment of the present disclosure.

FIG. 20A is a perspective view of an infra-red (IR) light-emitting diode (LED) circuit, according to an embodiment of the present disclosure.

FIG. 20B is a perspective view of an infra-red (IR) light-emitting diode (LED) circuit, according to an embodiment of the present disclosure.

DETAILED DESCRIPTION

Figure 1:
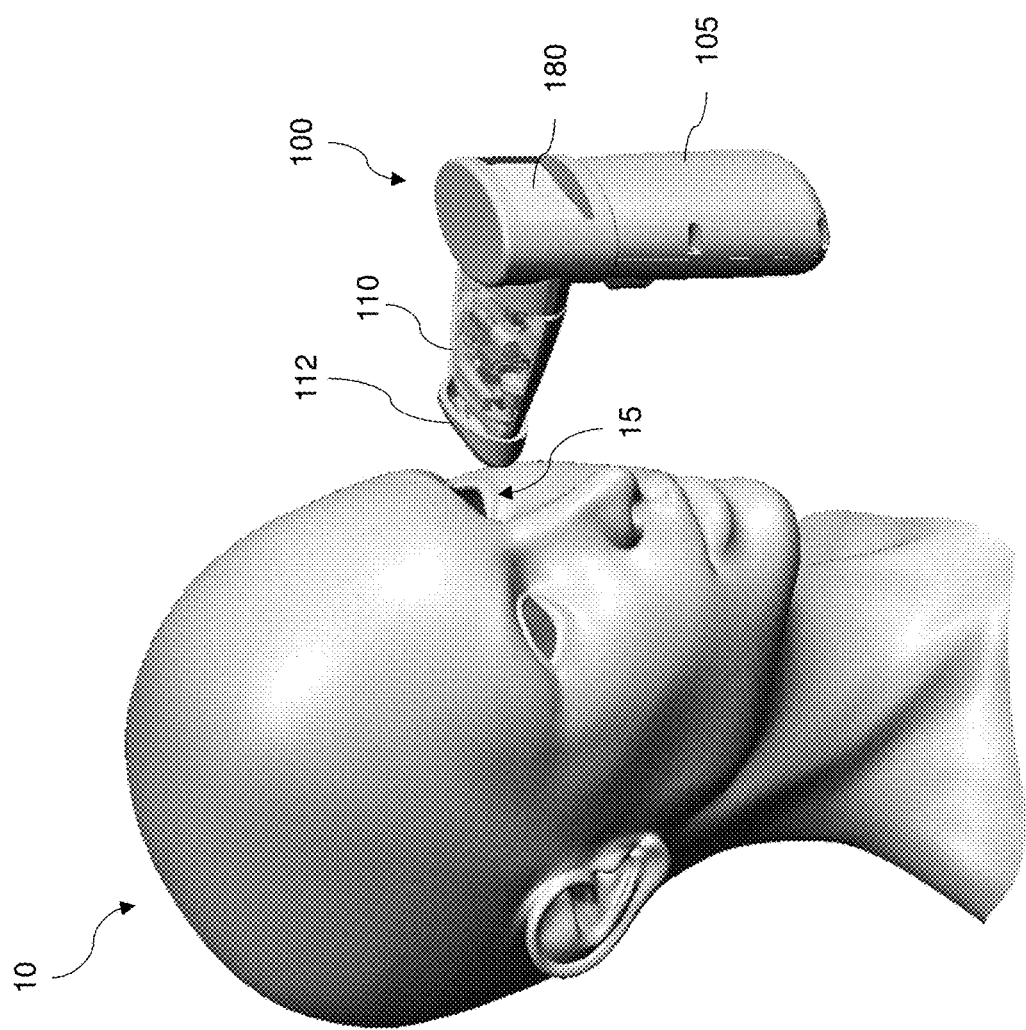
FIG. 1 is a perspective view of a gland treatment device, according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the therapeutic devices and systems are described in terms of heating the eyelids to treat MGD, it is understood that it is not intended to be limited to this application. The devices and systems are well-suited to any application requiring the glands of a patient. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring to FIG. 1, a gland treatment device 100 is shown positioned proximate to an eye 15 of a patient 10. In the illustrated embodiment, the treatment device 100 is configured for treatment of the Meibomian glands positioned within the patient's eyelids. However, it will be understood that the embodiments of the present disclosure may be adapted or suited for the treatment of other types of glands, pores, tissues, or other organs. The treatment device 100 includes a handle 105 sized, shaped, structurally arranged, and otherwise configured to be held or grasped by a human hand. In some aspects, the handle 105 may be configured to be grasped by the hand of the patient 10 and/or the hand of a physician. The handle 105 comprises a housing or enclosure that is coupled to another housing 110 extending transversely from the handle 105. The housing 110 is a protective enclosure that surrounds and protects various electrical and mechanical components that will be described further below. In some embodiments, the device 100 includes the housing 110, but not the handle 105. In some embodiments, the housing 105 is removable or detachable such that the handle 105 can be coupled or decoupled from the housing 110 based on the preferences of the person performing the treatment. For example, the handle 105 may be attached when the patient is performing the treatment themselves, or detached if a physician is applying the treatment. In other embodiments, the handle 105 is operantly attached to the housing 110. In some embodiments, the handle 105 houses or contains electronic and/or mechanical components, such as a battery, a speaker, haptic feedback actuators, image processing circuitry, or any other suitable electronic component described further herein.

A cup 112, which may also be referred to as a rest, a cover, or a stop, is coupled to a distal end of the housing 110. In the illustrated embodiment, the cup 112 comprises a relatively soft, compliant material, and includes a concave shape configured to be positioned against the patient's face around the eye and eyelids. In some embodiments, the cup 112 comprises an elastomeric material, such as silicone or rubber. In some embodiments, the cup 112 comprises a biocompatible material. Further, in some embodiments, the cup 112 comprises a film or coating configured to enhance the hygienic and sterile properties of the device 100.

As with acne or MGD, Meibum oils can become so clogged that a mechanical means of extracting a surface plug of high viscosity Meibum oil is necessary to free the production of new oils and restore flow. The device 100 includes a light-based heating element configured to direct beams of electromagnetic energy (e.g., IR light) to the patient's skin. When placed against the patient's eyelids, the device 100 may be configured to direct the energy to the Meibomian glands in the eyelids to warm up waxy oil or clogs within the glands so that the clogs can be expressed or otherwise removed. The best optimal therapeutic temperature is known to be 42 C whereas body temperature near the skin extremities can be as low as 32 C. In addition, or in the alternative, a massaging assembly can apply pressure to the eyelid tissue to help express the thick oil from the glands.

FIGS. 2A and 2B are different cross-sectional views of a distal portion of the device 100 shown in FIG. 1. As shown in FIG. 2A, the cup 112 comprises a rounded body with an opening sized and shaped to be positioned over the patient's eye. The device 100 includes a light element 120 that includes a plurality of light-emitting diodes (LEDs) configured to emit light through the opening of the cup 112. A rigid coupling member 124 is coupled to a distal surface of the light element 120. An optical waveguide 122 is attached to the coupling member 124. The waveguide 122 includes a material that is at least partially transparent, and in some embodiments extremely transparent (e.g., >95% % transmission), for the wavelengths of light emitted by the LEDs. In some embodiments, the optical waveguide 122 is secured to the coupling member 124 or to the light element 120 via magnets which allow it to be replaceable. The waveguide 122 comprises a concave shape on its distal surface to at least partially conform to the shape of the patient's eye and eyelids. As described further below, the waveguide 122 may be coupled to a massaging assembly such that an oscillating pressure can be applied to the patient's eyelids through the waveguide 122. In this regard, the waveguide 122 may comprise an elastomeric or compressible material that can conform to the curvature of the eye and more evenly distribute the application of pressure to the eyelid. Because the index of refraction of the material of the waveguide 122 is significantly greater than the index of refraction of the surrounding air, when the light is emitted into the waveguide 122 from the LEDs, the top and side surfaces can reflect any divergent light rays internally to reduce stray or wasted energy, similar to how fiber optic cables function due to total internal reflection.

The light element 120 is coupled to a heat sink 126 configured to absorb and disperse heat. Referring to FIGS.

2A and 2B, the heatsink 126 with air fins comprises a thermal manifold that is directly attached to a circuit board 125 of the light element 120 such that the heat sink exchanges the heat generated by the LEDs and/or the circuit board 125 of the light element 120 with air. In some embodiments, a solder or thermally conductive adhesive is used to attach the heat sink to the circuit board 125 and/or to the LEDs of the light element 120. Additionally, a fan 127 is coupled to the heat sink 126 and is configured to direct the heated air through the channels of the heat sink manifold 126 and disperse heat generated by the light element 120 over the face of a person. Thus the wasted heat gives rise to a gentle warm air flow over the face of the person that is pleasant.

The light element 120 may comprise an LED array, which may be attached via solder reflow to the circuit board 125, a flex circuit, or heat absorbing metal plates. In order to facilitate passing through the eyelids and targeting the Meibomian glands, the LED array may utilize a peak wavelength emission range between about 900-1300 nanometers (nm). However, any suitable wavelengths can be used, including wavelengths within 25 nm of about 2000 nm. The array may take on any geometric form such as a one-dimensional array or two-dimensional array or other arrangement.

The shape of the waveguide component 122 may be tailored to each individual and be made of soft clear material such as silicone (for example a transparent silicone such as Nusil MED-6020) or a highly transparent elastic thermoplastic polyurethane (TPU) such as Ellastolan®, which may funnel light from the light element 120 towards the eyelid using internal reflection. In some embodiments, the waveguide 122 has two sections, one being a rigid component such as transparent polycarbonate such as Lexan® as well as a soft elastomer component. The waveguide 122 may efficiently deliver diffuse light. Referring to FIG. 2B, a massaging assembly comprising a motor 130 and a cam 132 is configured to cause the waveguide 122, with the light element 120, heat sink 126, and fan 127, to oscillate along a longitudinal direction (i.e. proximal to distal, and vice versa) of the device 100. In this regard, the motor 130 is configured to cause the cam 132 to rotate, where the cam 132 is abutting a cam follower 134. The motor 130 may be mechanically coupled to the cam 132 using gears, belts, chains, or any suitable mechanical component. In the illustrated embodiment, the cam 132 comprises a cylindrical body that is rotationally mounted off-axis. In other embodiments, the cam 132 may comprise a non-cylindrical shape, such as an elliptical shape. As the cam 132 rotates, a more projecting portion of the cam 132 pushes against the cam follower 134, causing the cam follower 134, the fan 127, the heat sink 126, the light element 120, and the waveguide 122 to move distally toward the opening of the cup 112. In the illustrated embodiment, the circuit board 125 of the light element 120 is slidably coupled to struts 136, which include springs positioned around posts or rods. Because the light element 120, waveguide 122, heat sink 126, and fan 127 are coupled to the cam follower 134, when the cam 132 actuates the cam follower 134, the circuit board compresses the springs of the struts as the circuit board 125 slides distally along the struts 136. As the cam 132 continues to rotate, a less projecting part of the cam 132 abuts the cam follower 134, and the springs of the struts 136 can expand to return the circuit board 125, light element 120, and waveguide 122, back to their initial location. This is repeated for several rotations, creating an oscillating motion of the waveguide 122 relative to the patient's eye. As explained further below, in some embodiments, the massaging assembly can cooperate or function with a scleral lens-shaped eye cover to protect the cornea and direct the oscillating forces to the eyelid and reduce or eliminate the amount of oscillating force applied to the eyeball. In some embodiments, the massaging assembly comprising the motor 130, the cam 132, and the cam follower 134, is configured to cause the waveguide 122 to oscillate with a frequency of between 0.1 Hz to about 100 Hz. In an exemplary embodiment, the massaging assembly is configured to cause the waveguide 122 to oscillate with a frequency of between 0.5 Hz and 2 Hz.

In some embodiments, the cam follower 134 includes a sloped surface to introduce an additional rocking or tilting motion to the longitudinal oscillating motion. In that regard, as the more projecting part of the cam 132 impinges upon the sloped surface, an oscillating tilting motion is introduced that causes the distal surface of the waveguide 122 to thrust upward as the waveguide 122 projects distally, and then tilts downwards as the waveguide 122 retracts proximally. In other embodiments, the rocking motion may cause the waveguide 122 to thrust downward as the waveguide 122 projects distally.

It will be understood that a variety of additions, substitutions, or other modifications can be made to the embodiments of FIGS. 2A and 2B without departing from the scope of the present disclosure. For example, in some embodiments, the cam 132 is directly attached or positioned around an axle of the motor 130. In some embodiments, a servo is used instead of a rotating motor to actuate the massaging assembly. In some embodiments, the cam 132 directly abuts the fan 127, heat sink 126, or light element 120. In some embodiments, the massaging assembly is configured to cause only the waveguide 122 to oscillate, or only the waveguide 122 and the light element 120 to oscillate. In some embodiments, no heat sink 126 and/or fan 127 is used. In some embodiments, a light source other than LEDs is used to emit light, such as a laser, an incandescent bulb, or any other suitable light source. In some embodiments, the struts 136 do not comprise springs. In some embodiments, the struts 136 comprise compressible members in lieu of springs. In some embodiments, the springs are configured to expand when the waveguide 122 and light element 120 moves distally. In some embodiments, the cup 112 is integrally formed with the housing and comprises the same material that forms the housing. In some embodiments, the cup 112 is attached to the housing 110 by an adhesive, an interference fit, or is over-molded onto the housing 110. In some embodiments, the distal surface of the waveguide 122 is not curved, but planar or flat.

FIG. 3 is a partial cut-away view of a distal portion of a Meibomian gland treatment device 100, according to another embodiment of the present disclosure. In this regard, the device 100 further includes posts 142a, 142b, protruding upward from corresponding surfaces 144a, 144b of the housing 110. As explained further below, the posts 142a, 144b are configured to engage and couple to corresponding notches or holes of a scleral cover such that the housing 110 of the device 100 is held static relative to the scleral cover while the waveguide 122 is oscillating. In other words, in the illustrated embodiment, because the waveguide 122 is configured to move relative to the housing, the waveguide 122 is also configured to oscillate relative to the scleral cover. Accordingly, the waveguide 122 can compress the eyelid or other tissue between the waveguide and the scleral cover.

FIG. 3 further illustrates the LEDs 129 of the light element 120 positioned proximally of the waveguide 122. The LEDs 129 are configured to emit the light through the distal surface 121 of the waveguide 122. The distal surface 121 may have concave curvature in at least one direction. In the illustrated embodiment, the distal surface 121 is curved along two directions: a transverse direction between the posts 142a, 142b, and an elevation direction (i.e. upward and downward). This curvature may be described as matching the shape of a sphere, spheroid, or other curved three-dimensional shape. The curvature of the waveguide 122 may be configured for the particular therapy of interest. In the case of Meibomian gland therapy, the curvature of the distal surface 121 of the waveguide 122 is configured to match the shape of the patient's eye and eyelids.

The device 100 further includes an imaging component 160 configured to obtain images of the tissue during treatment. The imaging component 160 may include a digital camera sensor, such as a CCD. In the illustrated embodiment, the imaging component 160 is tilted downward and aimed to obtain images of the Meibomian gland. This camera could be for example, the OmniVision OVM6211. Such cameras can be implemented in a low-cost, mass produced, and/or small form factor grayscale imaging system-on-chip camera system less than 4 mm$^2$. In some embodiments, the imaging component 160 can be configured to take a picture of the eye with an infrared LED to validate the presence or absence of the scleral cover 150. Such cameras can be specifically designed for close-up pictures of the eye for eye tracking applications with a wide field of view and focal ranges from 10 mm-25 mm.

In other embodiments, the imaging component can be tilted, angled, focused, and otherwise configured to obtain images of the tissue or gland of interest. In some embodiments, the device 100 further includes image processing circuitry to generate images based on the image data obtained by the imaging component 160. The imaging component 160 and/or image processing circuitry can be in communication with a screen or display to output the images. In some embodiments, the display is coupled to the device 100 itself. For example, the images may be output to a screen on the rear face 180 of the housing 110, as shown in FIG. 1. In some embodiments, the device 100 is configured to output images to a separate display by a wired or wireless connection. For example, an industry standard bus or wireless protocol may be used to output the images, such as universal serial bus (USB), Bluetooth®, Wi-Fi, ultra-wide band (UWB), or any other suitable communication standard.

Figure 4:
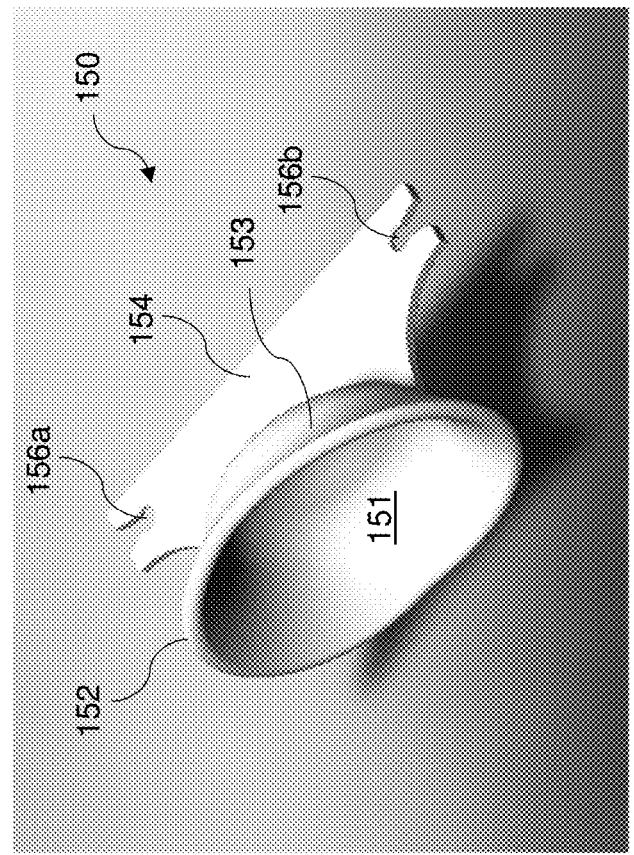
FIG. 4 is a perspective view of a scleral cover, according to an embodiment of the present disclosure.

FIG. 4 is a perspective view of a scleral lens-shaped cover or eye shield 150 used in conjunction with the gland treatment device 100. The eye cover 150 includes a protective cover portion 152 and a coupling feature or tab 154 configured to couple to a corresponding coupling feature (e.g., posts 142a, 142b) of the device 100. The tab 154, which may also be referred to as a bracket, comprises notches 156a, 156b configured to engage the posts 142a, 142b of the device 100. The tab 154 rests on the corresponding surfaces 144a 144b. The cover portion 152 of the scleral cover 150 includes a curved body configured to fit over or around the eye and make contact on the sclera part of the eye, as further described below with respect to FIG. 6 which shows a scleral lens. Both a scleral lens and an acrylic eye shield are typically very similar in shape but are different in their transparency. The cup shape of the depicted scleral lens cover 150 is similar to both a standard scleral lens as well as acrylic eyeshields, which vaults over the cornea to protect it. A scleral lens is transparent and allows for corrective vision whereas an eyeshield is typically opaque and reflects impinging radiation. While similar in shape, a scleral lens typically has a smaller diameter of 16-18 mm whereas an acrylic eyeshield is slightly larger to reduce lateral motion and can be about 20 mm to 25 mm across. In order to protect the cornea and eye from the LED light, a white TiO2 pigment can be included as an additive to an acrylic molded eyeshield. In some aspects, the additive can allow for all or a portion of impinging light to be reflected. However, the eye shield 150 for this device can be smaller in some embodiments than those typically used for radiation treatments. For example, in some embodiments, the scleral eye shield or eye cover 150 may have a diameter of approximately 18 mm. Mechanical holes and posts interlock and keep the relative position of the shield 150 from moving relative to the massaging optical waveguide 122 and the LED light elements. Thus, even if the shield 150 has room to laterally move on the surface of the eye, the LED light can still be reflected by the shield.

The cover portion 152 includes an inner surface 151 configured to be placed facing the patient's eye, and an outer surface 153 facing away from the eye. The scleral cover may comprise a biocompatible polymer that can protect the eye from radiation emitted by the light element 120. For example, in some embodiments, the scleral cover 150 comprises a rigid gas polymer (RGP). The RGP material may have a refractive index typically between 1.41-1.49. Being relatively rigid, such polymers have a softening point typically above 100° C. and more commonly above 150° C., whereas dielectric coatings can be deposited in some systems at temperature at or near room temperature minimizing any coefficients of thermal expansion mismatch during the coating process.

In some embodiments, the scleral cover 150 is made from biocompatible acrylic or poly(methyl methacrylate) (PMMA), which is widely used and accepted for eyeshields or prosthetic eyeballs and may further include a biocompatible smooth coating on the outer surface 153 and/or the inner surface 151. For example, a coating on the outer surface 153 may be a reflective coating having a high coefficient of reflectance for the wavelengths emitted by the light element 120. In some embodiments, the PMMA may include a formulation that incorporates an additive of titanium dioxide which will give the shield a white color and reflect infrared LED light very efficiently keep the eye safe from too much light exposure In some cases, such as for a home treatment device, users may wish to see through the protective scleral shield. There may be an additional dielectric coating. In some embodiments, the coating allows at least some visible light in the range of about 400-700 nm to be transmitted allowing for a user to see during treatment while reflecting infrared light heating the Meibomian gland. Thus this coating may allow for transparent materials to be used for the scleral cover, such that visible light passes through it, thereby enabling a person to watch TV, use their smartphone, or read during treatment. Such coatings are sometimes referred to as "hot mirror" coatings and are commonly used in optic to block infrared radiation but allow for visible transmission. Furthermore, the dielectric coating may reflect light in the SWIR range between about 900-1300 nm over a range of incident impingement angles such as +/−45 degrees while still allowing for visible light transmission. For a target reflection range of only 900-1300 nm, substantial improvements over the angle of incidence (AOI) and residual transmission can be realized. Each coating can be optimized based upon the exact wavelength specifications and requirements.

It should be noted that the scleral cover 150 may also have an outer protective coating placed over the dielectric reflection layer and/or directly over the inner surface 151 of the scleral cover 150 in order to provide smooth protection to the eye. Typically, the dielectric coating is composed of alternating layers of high and low index oxide materials which are not water loving and would not feel slippery inside the eye. Thus, a protective coating may be included such as a coating known as Hydra-Peg® as an example, which is hydrophilic coating (composed of over 90% water) that has been shown to significantly increase the comfort level of contact lenses.

Accordingly, the scleral cover 150 provides for multiple types of protection to the patient. While wavelengths between 900-1400 nm may be considered safe from an optical safety perspective, the scleral cover or lens 150 may provide additional protection through the corneal pathway due to a "hot mirror" dielectric coating or titanium dioxide (TiO2) incorporated into the material forming the scleral cover 150. In addition, the scleral cover 150 provides mechanical back pressure pinching the Meibomian glands and pressure isolation over the eyeball. Further, the scleral cover 150 provides thermal conduction safety by isolating the cornea from the tissues being heated by the device. Further, as Meibomian gland oils are extruded, the scleral cover 150 may also prevent these oils from coating the cornea and mixing into the tear fill which can cause discomfort. These oils can be cleaned off after treatment when the scleral covers are washed. A scleral cover cleaning solution can be sold as a separate consumable with proper additives to dissolve Meibomian gland oils and clean the lens. In other embodiments, the scleral cover 150 comprises a disposable, consumable item that is intended for single use. In addition, a standard storage solution can be used as a separate consumable during insert of the scleral cover 150 which also has tear film formulations that repair corneal epithelial growth, such as an aqueous hyaluronic sodium additive solution.

In some embodiments, the scleral cover 150 includes other coupling or attachment features instead of or in addition to the notches 156a, 156b. For example, in some embodiments, the coupling features include one or more holes in the tab 154. In other embodiments, a latching feature, such as an inclined projection can be included on the cover 150 to connect to a corresponding latching feature coupled to the housing 110 of the device 100. In other embodiments, magnets, grooves, slots, and/or any other suitable coupling feature is used. In some embodiments, the shape of the tab 154 itself is a coupling feature. For example, in some embodiments, the tab 154 may be shaped to fit within a corresponding recess of the housing 110. In other embodiments, an interference fit is used. In other embodiments, the scleral cover 150 does not include a coupling feature. In some embodiments, the scleral cover 150 includes only the cover portion 152.

Figure 5:
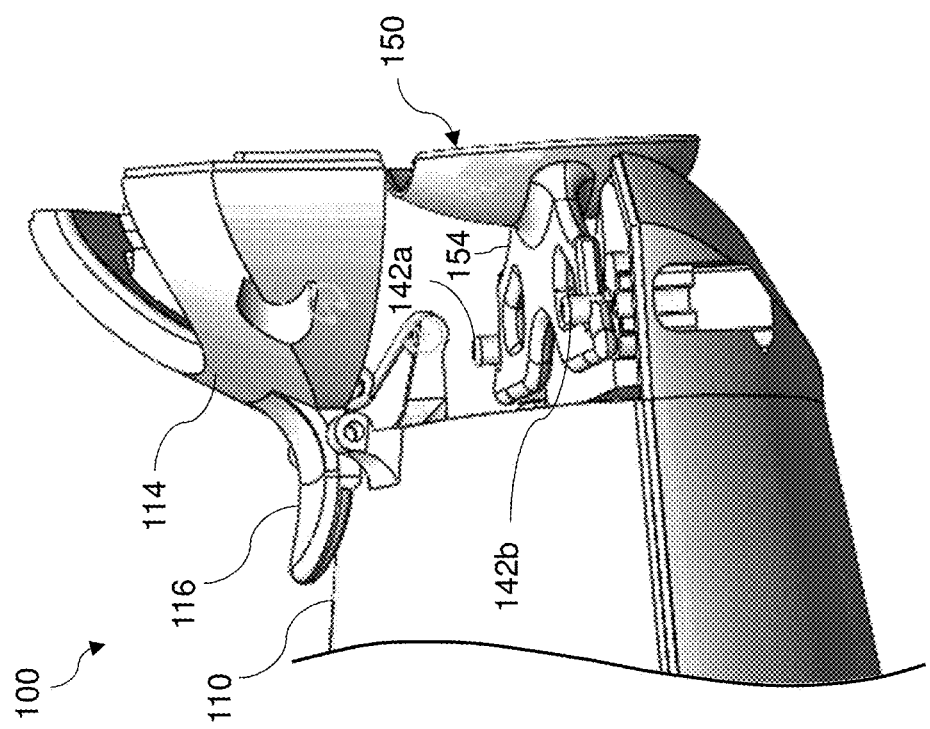
FIG. 5 is a perspective view of a scleral cover coupled to a housing of a gland treatment device, according to aspects of the present disclosure.

FIG. 5 is a perspective view of a scleral cover 150 coupled to a gland treatment device 100, according to an embodiment of the present disclosure. The scleral cover 150 is coupled to the housing 110 of the device 100. Referring generally to FIGS. 4 and 5, the notches 156a 156b in the tab 154 of the scleral cover 150 engage corresponding posts 142a, 142b protruding from surfaces of the housing. In some embodiments, the notches 156 and/or posts 142 are differently shaped to ensure that the scleral cover 150 is coupled to the device 100 in a particular orientation. In some embodiments, the scleral cover 150 is symmetrical such that the cover 150 can be installed in either orientation.

In the embodiment of FIG. 5, the housing 110 further includes a clamp 114 configured to open and close to clamp on the tab 154 of the scleral cover 150 by a hinge mechanism. In some embodiments, the clamp 114 can be opened by a user using a locking feature 116. In some embodiments, the clamp 114 comprises a bi-stable clamp. In this regard, the scleral cover 150 may comprise a single use or disposable component that can be thrown away after being used for a patient. A new scleral cover 150 can be coupled to the device 100 by opening the clamp 114, placing the tab 154 on the surface of the housing 110 to engage the posts 142a, 142b, closing the clamp 114 on the tab 154, and pushing the locking feature 116 to a locked position to keep the clamp 114 from opening inadvertently. Other locking features are also contemplated, including latch connections, magnetic connections, or any other suitable locking feature.

Figure 6:
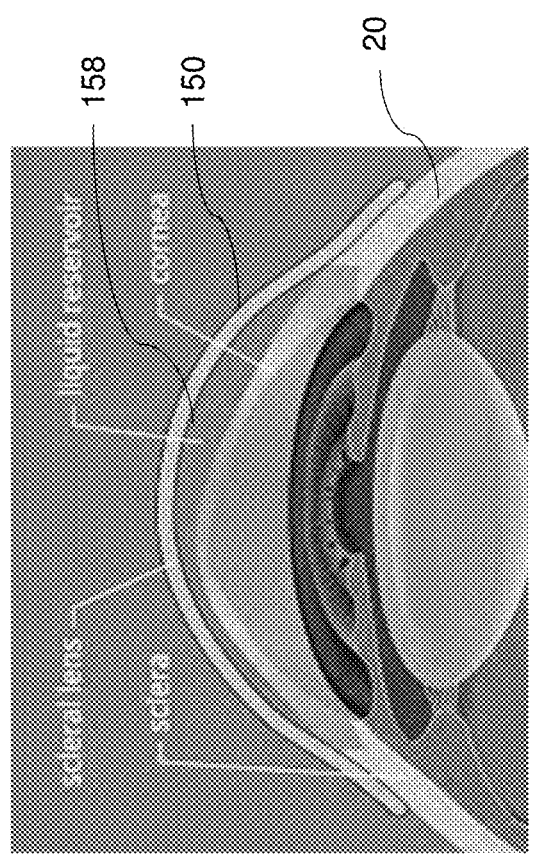
FIG. 6 is a cross-sectional view of a scleral cover positioned over a patient's eye, according to an embodiment of the present disclosure.

FIG. 6 is a cross-sectional view of a scleral cover 150 positioned over a patient's eye 20. In the illustrated embodiment, the scleral cover 151 further includes a liquid reservoir 158 coupled to an interior surface of the cover 150. The liquid reservoir may advantageously prevent the interior surface of the cover 150 from coming in direct contact with the patient's cornea. This may improve patient comfort, reduce abrasion or damage to the surface of the cornea, and further reduce the amount of heat that is transferred to the tissues of the eye 20. In some embodiments, a different material or component is used instead of the liquid reservoir 158. For example, a gel layer may be positioned over the interior surface of the scleral cover 150, in some embodiments. In other embodiments, no reservoir or spacing element is used. Instead, the cover is sized and shaped such that, when positioned over the eye 20, there is an air gap between the interior surface of the cover 150 and the cornea of the eye 20. Typically, this gap can be as large as 500 microns or more typically 300 µm in the center of the contact lens. Other vaulted gaps are possible to provide additional thermal isolation. Based on finite element analysis (FEA), these thermal gaps allow for heating of the Meibomian glands over a certain time period, typically between 2-5 minutes while the cornea safely maintains a temperature below 39 C. With the appropriately chosen wavelength LEDs, heating times to get up to the desired temperature for the Meibian gland of 42 C may be in as little as 30 seconds due to direct penetrating absorption of the IR LED light in the glands. The thermal barrier the scleral shield provides is important for delaying heat transmission because above approximately 39 C at the cornea patients may start to notice thermal pain.

Figure 8:
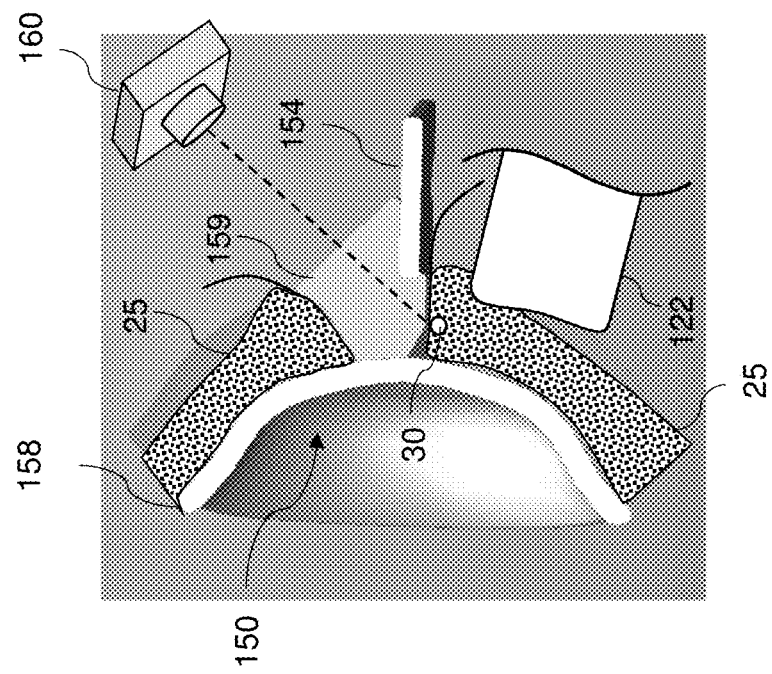
FIG. 8 is a cross-sectional view of the scleral cover shown in FIG. 7, according to an embodiment of the present disclosure.
Figure 7:
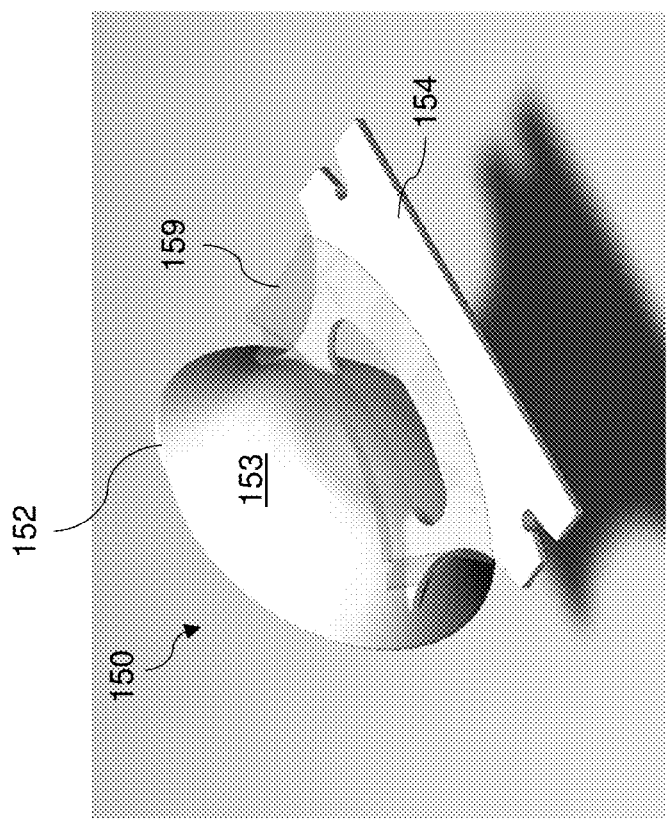
FIG. 7 is a perspective view of a scleral cover that includes an angled viewing window, according to an embodiment of the present disclosure.

FIG. 7 is a perspective view of a scleral cover 150, according to another embodiment of the present disclosure. FIG. 8 is a cross-sectional view of the cover 150 shown in FIG. 7, while the cover 150 is being worn by a patient during a therapeutic procedure. The scleral cover 150 shown in FIG. 7 includes many of the same components as the embodiment shown in FIG. 4, including a cover portion 152, a tab 154, and an outer surface. Additionally, the scleral cover 150 shown in FIG. 7 includes an angled window attached to the tab 154 and cover portion 152. The angled window comprises an optically transparent, or partially transparent material that is sloped toward the tab 154. The angled window 159 includes at least one angled flat, or substantially flat surface to provide a view of the Meibomian glands to a user and/or an imaging component 160. As shown in FIG. 8, the imaging component 160, which may be a component of the device 100 as shown in FIG. 3, is configured to obtain images of the Meibomian glands 30 during the treatment. Thus, while IR light and massaging pressure is applied to the eyelid 25 by the waveguide 122, the imaging component 160 can be used to monitor the treatment and determine whether and to what extent clogs are being removed or expressed from the gland 30. Thus, in some aspects, it may be beneficial for the window 159 to include flat viewing surfaces to reduce or remove distortions in the image. However, in other embodiments, one or more surfaces of the window 159 are curved. For example, in some embodiments, the curvature of the surface(s) of the window 159 may allow for some magnification of the image of the gland 30.

Figure 9:
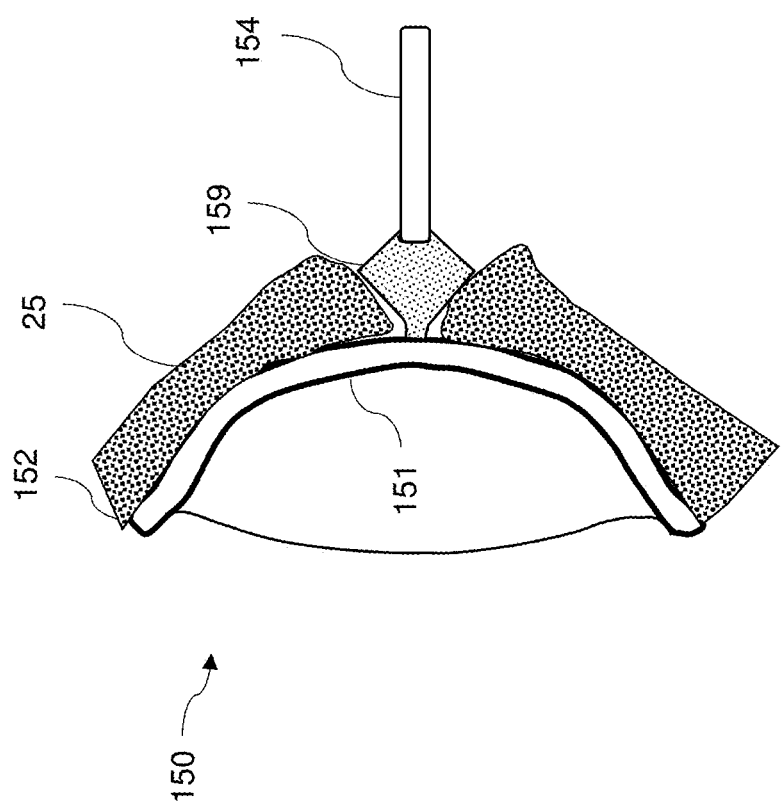
FIG. 9 is a cross-sectional view of a scleral cover that includes an angled viewing window, according to another embodiment of the present disclosure.

FIG. 9 is a cross-sectional view of a scleral cover, according to another embodiment of the present disclosure. The scleral cover 150 shown in FIG. 9 includes similar components as described above with respect to FIGS. 7 and 8. In the embodiment of FIG. 9, the window 159 is a bi-directional window, such that angled surfaces are present both above and below the tab 154. In this manner, the cover 150 can be left in place and in the same orientation, while the device is decoupled from the cover 150, rotated 180 degrees, and then recoupled to the cover 150 to continue treatment on the glands of the other remaining top or bottom eyelid.

Figure 10:
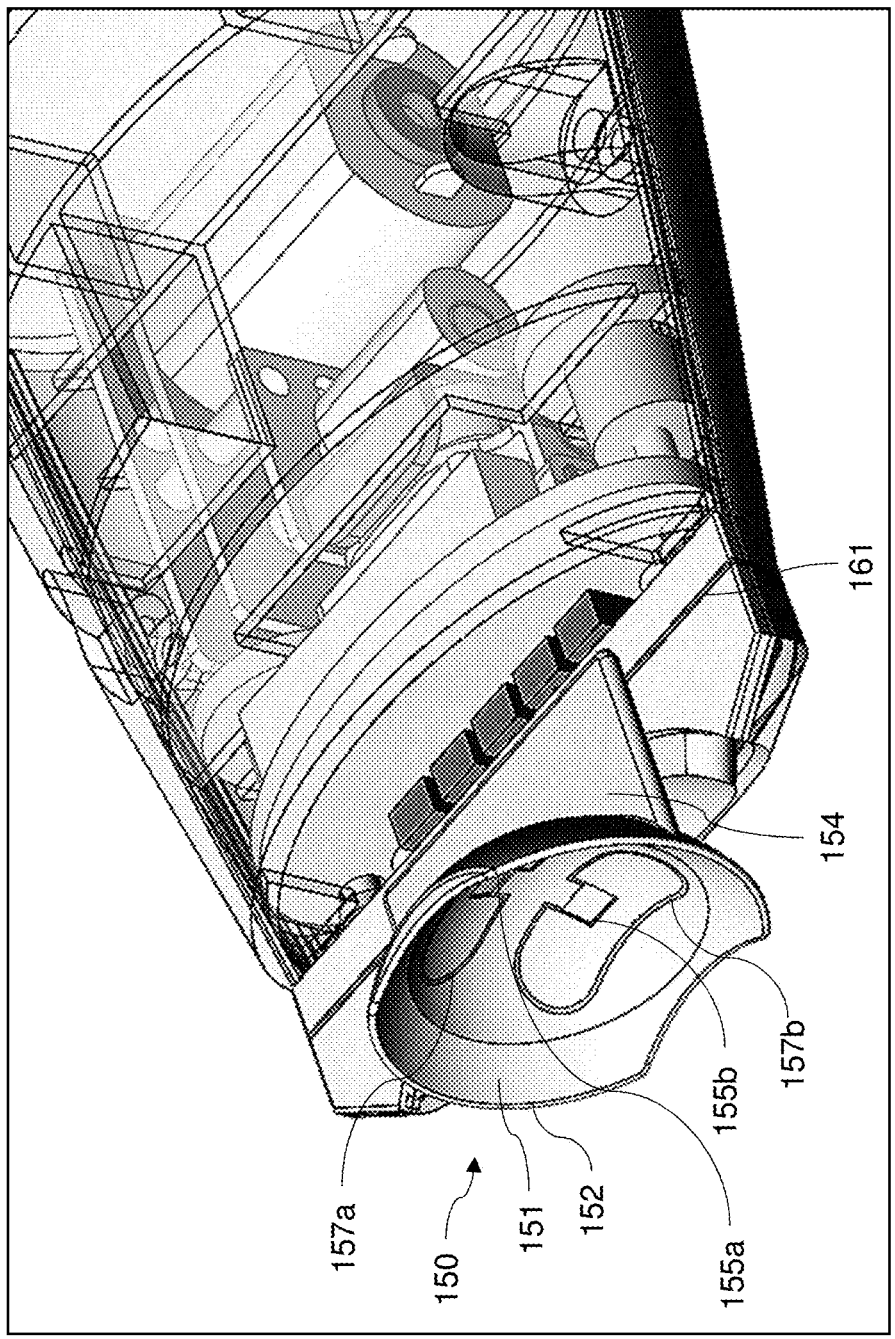
FIG. 10 is a partially transparent perspective view of a scleral cover having an integrated temperature-sensing circuit coupled to the housing of the gland treatment device, according to an embodiment of the present disclosure.

In some aspects, it may be desirable for the scleral cover 150 to include one or more electronic components, such as sensors, RFID identification chips, or other circuitry. For example, it may be beneficial to monitor the temperature of the surface of the eye, or the eyelid, using a temperature sensor incorporated into the scleral cover 150. Alternatively or additionally, it may be beneficial to include identifying tags or chips that can be used to ensure that (1) a scleral cover 150 is coupled to the device before treatment begins (2) the scleral cover is authentic or otherwise authorized for use, and/or (3) correct sensor calibration is applied to the readings of any sensors. In this regard, FIG. 10 illustrates a treatment device coupled to and in communication with a scleral cover having integrated temperature sensor ASIC circuit chips 155a and 155b for upper and lower eyelids and associated receiving antenna coils 157a and 157b. In one embodiment, the circuits comprise radiofrequency (RF) circuits that can be wirelessly powered via integrated receiving antennas 157a, 157b in the cover 150 which receives power from a read circuit in the handheld. The read circuit can include its own loop antenna 161 made from a wire positioned in in the nose of the device and in close proximity to the receive antennas 157a and 157b. In some embodiments, the antenna 161 is embedded within the housing 110 near the distal end, or nose, of the device 100. In some embodiments, the antenna 161 may comprise a metallic strip or ring that is positioned within a groove formed in the housing 110. In some embodiments, the antenna 161 may comprise a conductive trace deposited over the housing 110. Although passive NFC or UHF based RFID may be used, in one embodiment, UHF RFID tags are used inside 150, as close range UHF involves single coil antennas 157a or 157b for adequate wireless communications of the ID and temperature. One example of a UHF RFID chip less than 2×2 mm square in size and contained within the shield is the EM microelectronic ASIC chip EM4325. Each circuit includes a loop antenna configured to harness wireless power supplied by a wireless communication module coupled to or contained within the housing 110 of the device 100 and transmitted via a loop antenna 161 in the housing nose. In one embodiment, an RFID temperature-sensing circuit is used, where the signal returned by the circuitry in the cover 150 includes identifying information and temperature information. For example, the signal returned by the RFID temperature-sensing circuit may comprise a series of bits, where the first or last bits in the signal indicate the temperature.

Accordingly, in some embodiments, a single antenna and/or circuit can be used for both device identification and temperature sensing without direct electrical contact or battery power to the sensor. This affords a much thinner eye cover 150.

Figure 11:
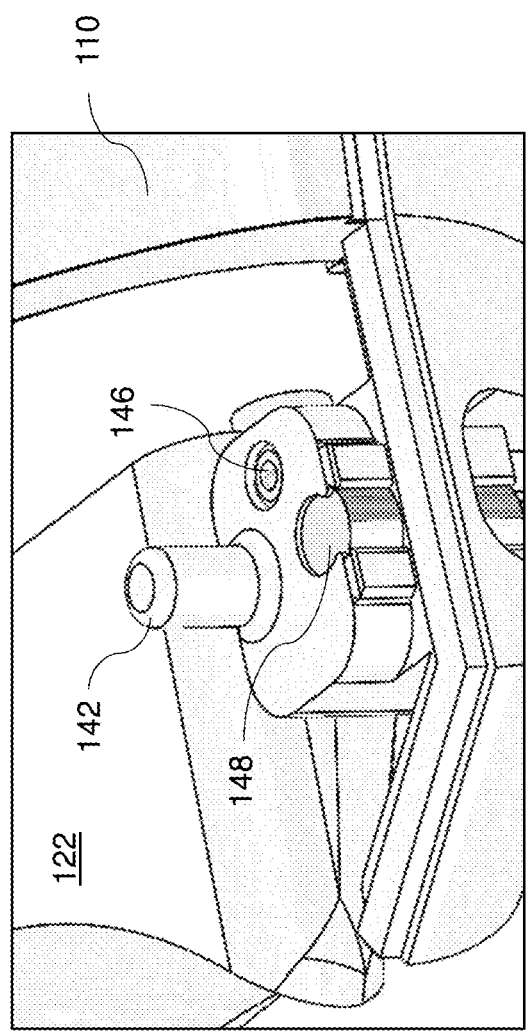
FIG. 11 is a perspective view of a coupling feature for establishing a mechanical and electrical connection between a gland treatment device and circuitry of a scleral cover, according to an embodiment of the present disclosure.

However, direct wired techniques may also be used for powering and communicating with any electronics of the scleral cover 150. For example, FIG. 11 illustrates a distal portion of a treatment device 100 that includes a magnetic attachment feature 148 and an electrical contact 146 positioned near the engagement post 142. The magnetic feature 148 may be used for securing the clamp 114 (FIG. 5) in a closed position, and/or for securing the tab 154 of the scleral cover 150 to the housing 110. In another aspect, the magnetic feature may be used as an electrical ground for electronic components in the scleral cover 150. In this regard, in some embodiments, the scleral cover 150 has a corresponding pad or other electrical contact configured to contact the electrical contact 146. Accordingly, a wired interface can be used to power the electronics of the scleral cover 150. In some embodiments, the electrical contact 146 comprises a pogo pin.

In the illustrated embodiment, the ASIC circuits 155a, 155b, and/or the receiving antennas 157a, 157b are mounted on the inner surface 151 of the cover 150. However, one or more of the electronic components may be coupled to, mounted on, or integrated within, any portion of the cover 150, including the outer surface and/or the tab 154. Additionally, in some embodiments, a plurality of electronic contacts is incorporated into the device 100. For example, two, three, four, six, eight, or more electrical contacts may be used. The contacts may be incorporated into any suitable surface or portion of the housing 110, particularly where the tab 154 of the scleral cover 150 contacts the housing 110, or any other portion of the device. In some embodiments, the contacts are formed within an electrical outlet that provides for mechanical and electrical communication between the electronics of the scleral cover 150 and the device 100. For example, the tab 154 of the cover 150 may form an electrical plug or jack (e.g., USB-style plug) that couples to a corresponding outlet of the device 100.

Figure 12:
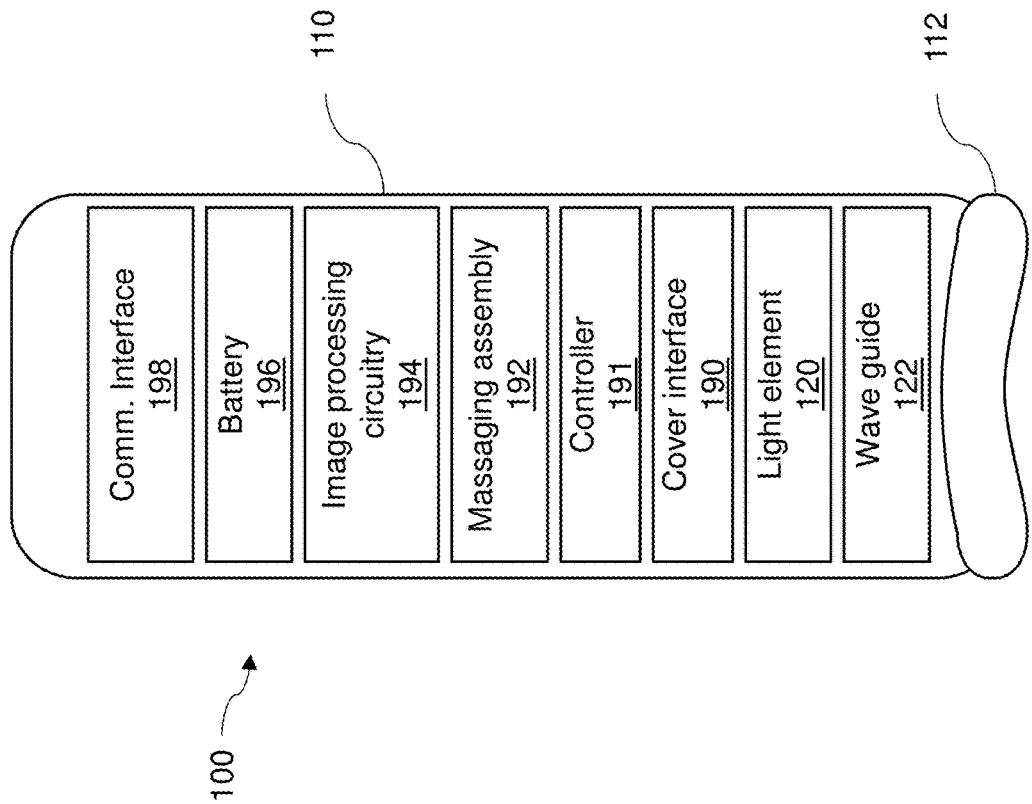
FIG. 12 is a diagrammatic view of a gland treatment device, according to an embodiment of the present disclosure.

FIG. 12 is a diagrammatic view of a gland treatment device 100, according to an embodiment of the present disclosure. The device 100 includes a waveguide 122, a light element 120, a cover interface 190, a controller 191, a massaging assembly 192, image processing circuitry 194, a battery 196, and a communication interface 198 coupled to or contained within a housing 110. A cup or rest 112 is coupled to a distal end of the housing 110. The waveguide 122 may be coupled to the light element 120 as described above, such that the light element is configured to deliver light (e.g., IR light) to the patient's eyelid through the waveguide 122. The waveguide 122 may comprise a transparent, or partially transparent material. The material of the waveguide 122 may also be soft, compliant, and/or flexible for added comfort and force distribution across the eyelid. The light element 120 may comprise a plurality of LEDs or other emitters coupled to a circuit board. In an exemplary embodiment, the emitters are aligned along a transverse axis to provide for a wide beam of light through the waveguide 122. However, other arrangements are also contemplated, including multiple rows of emitters, an annular arrangement of emitters, or any other suitable pattern or arrangement.

The cover interface 190 comprises circuitry to communicate with any electronic components of the scleral cover 150. In one embodiment, the cover interface 190 comprises a wireless transceiver or antenna configured to wirelessly power and communicate with a corresponding wireless circuit of the cover 150. In other embodiments, the cover interface 190 comprises a wired connection including one or more electrical contacts, sockets, outlets, or any other suitable form of wired communication circuitry. The cover interface 190 may be configured to direct signals received from the cover electronics to the controller 191, in some embodiments. The controller 191 comprises a microcontroller or processor in communication the components of the device 100, including the light element 120, the cover interface 190, the massaging assembly 192, the image processing circuitry 194, and the communication interface 198. In some embodiments, the controller 191 receives an operating voltage from the battery 196. In some embodiments, the controller 191 is configured to distribute electrical power from the battery 198 to other components of the device 100, including the light element 120, massaging assembly 192, and/or the cover interface 190. In some embodiments, a separate power supply is configured to distribute electrical power. In some embodiments, the battery 196 is configured to provide power in the range of 1-10 Watts. In some embodiments, a further battery is configured to couple to the device 100 by the communication interface to provide additional power during treatment.

The controller 191 may be in communication with a user input, such as a button, capacitive touch sensor, switch, a dial, or any other suitable user input device. The controller 191 may be in communication with a memory device comprising executable instructions or software for operating the components of the device 100. For example, in response to receiving the input from the input device, the controller 191 may control the light element 120 and/or the massaging assembly 192 to initiate a therapeutic protocol. The protocol may comprise instructions to apply the light from the light element 120 and/or massaging pressure from the massaging assembly 192 for a predetermined amount of time, at a predetermined intensity, and/or a predetermined frequency. In some embodiments, the controller 191 is configured to adjust an operating parameter of the protocol, such as intensity of the light or the speed of the massaging pressure, based on an input from the input device. In some embodiments, the controller 191 is configured to receive feedback from the sensors or other circuitry of the scleral cover 150 to control the therapeutic protocol. For example, the controller 191 may be configured to receive temperature data from a temperature sensor of the cover 150 via the cover interface 190. If the received temperature exceeds a predetermined threshold, the controller 191 may cause the light element 120 to decrease its output, or to stop emitting light. In some embodiments, the controller is configured to verify the presence and/or authenticity of a scleral cover as a precondition to performing the therapeutic protocol. For example, the controller 191 may be configured to compare an identification code from the scleral cover electronics to a database of identification codes to determine that the scleral cover 150 is authentic, authorized for use, and/or whether the scleral cover 150 has been used before.

The controller 191 may include one or more electronic drive current multichannel ASIC controllers that drive the individual emitters of the element 120 with control options for reducing heat load via duty cycle or turning on or off channels. The controllers may be small enough that they can be situated within the device housing or optionally also embedded in the tethered controller. An example of such a multichannel LED driver chip is the PCA9956B from NXP semiconductor with an I2C bus capable of driving up to 24 individual channels.

The massaging assembly 192 may comprise various electrical and mechanical components to provide an oscillating, massaging pressure to the relevant tissue of the patient. For example, the massaging assembly 192 may include an electrical motor, a solenoid, a cam, cam follower, and/or any other suitable component to move the waveguide 122 in an oscillating manner to massage the patient's eyelids. The massaging assembly 192 may be controlled by the controller 191 based on a predetermined protocol. For example, in some embodiments, the protocol includes instructions to power the light element 120 for an amount of time before activating the massaging assembly 192, thereby allowing the tissues and material in the Meibomian glands to warm up and soften before pressure is applied. In other embodiments, the massaging assembly 192 and the light element 120 are activated simultaneously.

The image processing circuitry 194 may include processing components to generate images or image data based on signals received from the imaging component 160. In some embodiments, the image processing circuitry 194 is part of the controller 191. In other embodiments, the image processing circuitry 194 comprises separate electronic components. The image processing circuitry 194 may output the images or image data to the communication interface 198. The communication interface may provide for wired and/or wireless communication with a computing device, such as a smart phone, tablet computer, laptop computer, desktop computer, or any other suitable computing device. In some embodiments, the communication interface 198 is configured to provide for communication with a display, such as a computer monitor or a television. The communication interface 198 may comprise an industry standard bus or wireless protocol, such as USB, HDMI, Bluetooth®, Wi-Fi, UWB, near-field communication (NFC), or one or more proprietary communication protocols. The battery 196 may comprise a rechargeable battery, such as a lithium-ion battery. In some embodiments, the battery 196 comprises a disposable non-rechargeable battery, such as one or more AA or AAA batteries.

Figure 13:
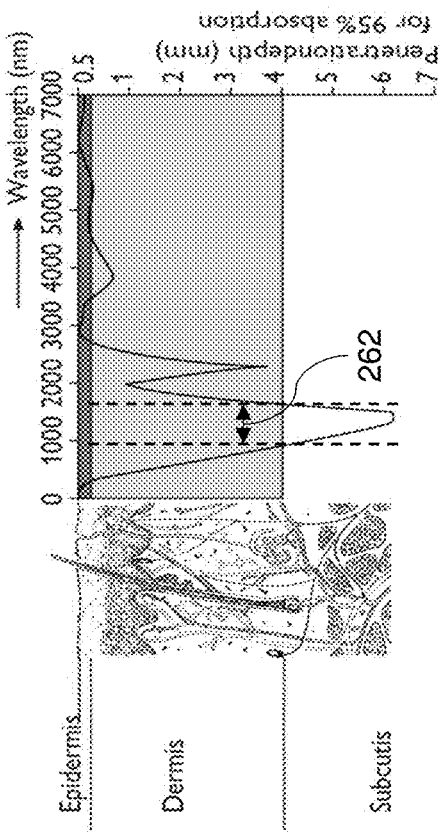
FIG. 13 is a graph of skin reflectance over a range of wavelengths of light, and for a variety of skin tones, according to aspects of the present disclosure.

The light element 120 is used to irradiate the relevant tissue (e.g., the eyelid and Meibomian glands) to cause the tissue to warm up. Aspects of the present disclosure provide light elements configured to operate at wavelengths that advantageously provide a number of benefits. In an exemplary embodiment, the light element 120 is configured to provide light having a center wavelength that is between about 950 nm and about 1050 nm. In one embodiment, the light element 120 is configured to emit light that has a center wavelength of approximately (e.g., +/−5 nm) 980 nm. In this regard, FIGS. 13-18 are graphs that illustrate the optical properties (e.g., reflectance, absorption, transmission) and interactions of various wavelengths of light with different tissues and materials. For example, FIG. 13 is a graph 210 that shows the reflectance of different wavelengths of light for three different skin tones. In this regard, it may be beneficial to irradiate the skin with wavelengths of light that interact with different skin tones similarly. As shown illustrated by the lines 212, 214, and 216, light within the range of about 950 nm to about 1,000 nm exhibits relatively lower reflectance for all three skin tones, and the difference in reflectance between the skin tones in the range between lines 212 and 214 is not as significant as the difference in reflectance for wavelengths smaller than 950. Further, light greater than about 1150 (illustrated by line 216), also shows low reflectance and low variation.

In another aspect, the efficiency of light profiles of light emitters having different peak wavelengths can vary. For example, the intensity of light from LEDs having peak wavelengths near 1000 nm exhibits improved relative optical intensities for the same drive power. This wavelength range may be very energy efficient for both AlGaAs and InP based LEDS. In addition, AlGaAs 980 nm LEDs are lower cost to manufacture compared with InP LEDs typically made for higher wavelengths.

Figure 15:
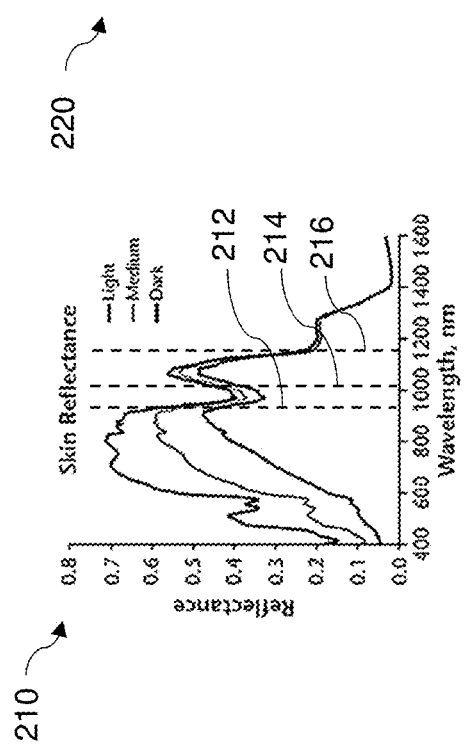
FIG. 15 is a graph of transmission and absorption of the retina of a human eye over a range of wavelengths of light, according to aspects of the present disclosure.
Figure 14:
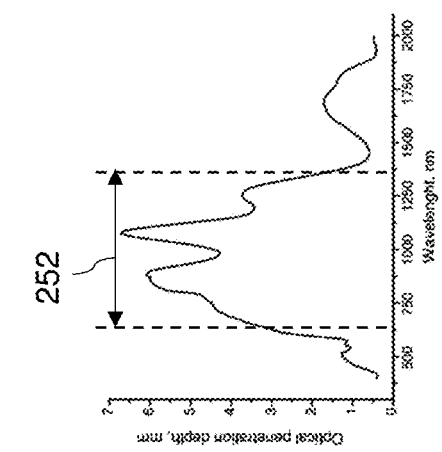
FIG. 14 is a diagram illustrating an optical penetration depth of human skin over a range of wavelengths of light, according to aspects of the present disclosure.
Figure 16:
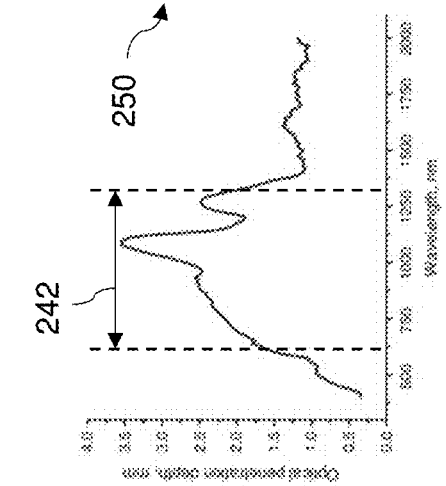
FIG. 16 is a graph of optical penetration depth of human skin over a range of wavelengths of light, according to aspects of the present disclosure.
Figure 17:
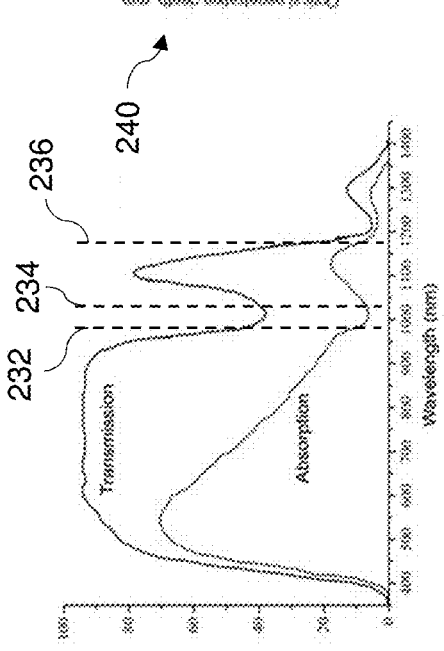
FIG. 17 is a graph of optical penetration depth of human mucous tissue over a range of wavelengths of light, according to aspects of the present disclosure.

FIGS. 14-17 generally illustrate the absorption and penetration depths of different wavelengths. For example, FIG. 14 is a graph 220 that shows that the wavelengths between about 950 nm and about 1300 nm exhibit deep absorption in the skin, at 4 mm or deeper. FIG. 15 is a graph 230 illustrating the transmission and absorption of different wavelengths of light by to and by retina. In this regard, there is both a drop in transmission to the retina and a drop in direct retinal absorption of light having wavelengths between about 970 nm (line 232) and about 1030 nm (line 234). Further, wavelengths greater than 1170 nm (line 236) also show relatively low (e.g., at or below 15%) transmission and absorption. FIGS. 16 and 17 are graphs 240, 250, that illustrate the optical penetration depth for various wavelengths of light in human skin and underlie human mucous or interstitial tissue, respectively. Because the Meibomian glands may reside at depths of about 2.0 mm or deeper and most eyelids are in the range of 3.5 mm-4.5 mm in total thickness, it may be beneficial for the emitted light to comprise wavelengths whose penetration depths in skin and mucous tissue are greater than about 2 mm. As shown in both graphs 240, 250, wavelengths in the ranges 242 and 252, which spans between about 750 nm to about 1250 nm, have optical penetration depths of greater than 2 mm, and as deep as 3.5 mm for skin and 6.5 mm for mucous tissue.

The graphs above illustrate the benefits of using an IR light source with a center frequency that is between about 950 nm to about 1000 nm. In an exemplary embodiment, an IR LED having a center frequency of about 980 nm may combine the benefits of relatively low reflectance in the skin, low variation of different skin tones, low retinal absorption, and deeper penetration depths to optimize the effectiveness of the light source in warming the tissue reducing or eliminating potential damage to the eye as well as low cost.

From a safety perspective the outer epidermis layer of skin has sensitive thermal nerve receptors that when heated above about 43° Celsius (C) give rise to pain, the eyelids being an especially sensitive area of skin. However, in most cases of MGD, the temperature rise necessary to unclog and induce new flow of Meibomian gland lipid oils is about 42° C. There is thus a narrow treatment window that is highly effective and pain free. In addition, the cornea and lens in the eye are also very sensitive to temperature and should remain below about 39° C., as the cornea can start to feel pain above about 40° C. Prolonged temperatures above this range are associated with a condition called Glassblower's cataract that is caused by prolonged infrared heating of the cornea and lens work. The embodiments disclosed herein address these safety considerations, especially for a home-based treatment, using protective scleral covers, for example.

The present disclosure contemplates additional or alternative configurations, form factors, and features for gland treatment devices other than those described above. For example, FIG. 18 is a perspective view of a patient 10 with a wearable gland treatment device 300 positioned over the patient's eyes with an eyeglass frame form factor. The treatment device 300 is coupled to or mounted on an eyeglass frame 310, such that the treatment device 300 can be worn by the patient 10 while the therapeutic procedure is being performed. FIG. 19A is a front view of the device 300 shown in FIG. 18, with the device 300 mounted on a top portion of the eyeglass frame 310. FIG. 19B shows a light element 320 of the device 300 shown in FIG. 19A. The light element 320 includes a plurality of LED bulbs or elements in a curved or focused arrangement, such that the emitting axes of the individual elements intersect. In an embodiment, the individual LEDs are arranged with respect to one another such that their respective emitting axes intersect at the treatment site (e.g., the eyelid). The LED array elements may be arranged to be focused onto a given region of the eyelid by using different LED elements pointed at different angles onto the same spot such that optical flux is concentrated or focused at the Meibomian glands or a particular Meibomian gland. Arrays of linear LEDs may target each array of Meibomian glands simultaneously yet have multiple LED rows arranged at different angles to target a single Meibomian gland.

FIGS. 20A and 20B are different perspective views of a light element 320, according to embodiments of the present disclosure. The light element 320 includes a plurality of individual emitters 329, such as LEDs, arranged in two rows and mounted on a circuit board 325. The circuit board 325 is configured to connect to a controller and/or power source of a gland treatment device (e.g., 100, 300). Each emitter is configured to emit light within an angular dispersion or distribution 360. Each emitter may comprise a lens or other optical component to focus the spread of the light to a particular angular range.

Figure 21:
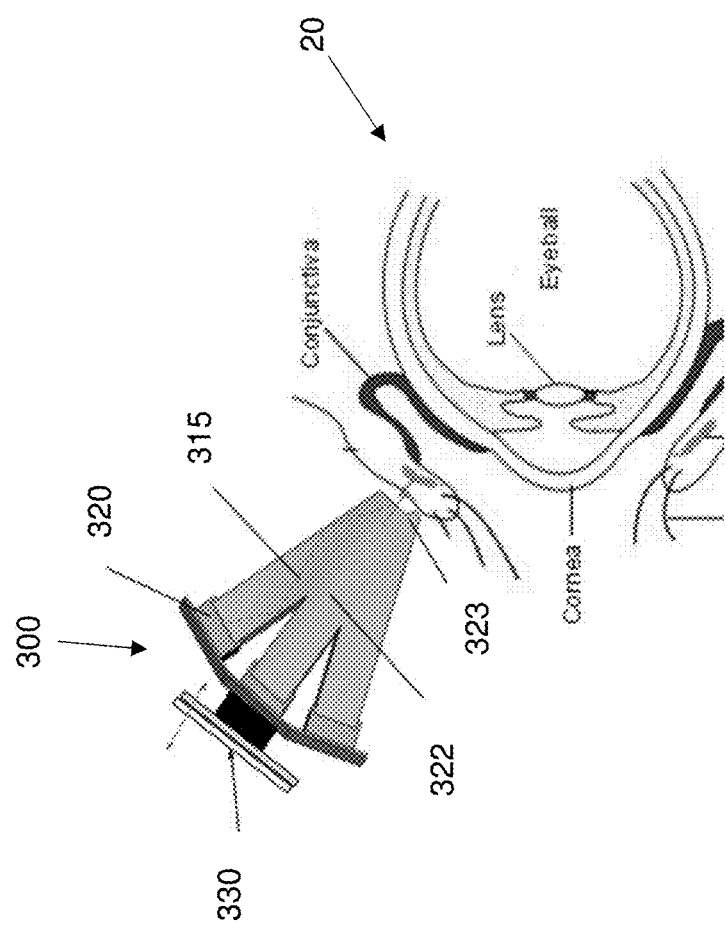
FIG. 21 is a diagrammatic view of an IR light element and biomorph actuator irradiating a human eyelid, according to an embodiment of the present disclosure.

FIG. 21 illustrates a portion of a wearable gland treatment device, according to an embodiment of the present disclosure. The device 300 includes a light element 320 having a plurality of LEDs arranged in a curved pattern, similar to the embodiment shown in FIG. 19B. A waveguide 322 is coupled to the light element 322 and is configured to direct light from the light element 320 to the eyelid. As above, the waveguide 322 optimally includes an elastomeric material. For example, in some embodiments, the waveguide 322 comprises silicone or elastic polyurethane material The device 300 further includes an actuator 330 configured to cause a vibrating or oscillating motion, as similarly described above. In some embodiments, the actuator 330 comprises a biomorph actuator. In some embodiments, the actuator 330 comprises a piezoelectric component, a microelectromechanical component, a solenoid, a motor, or any other suitable type of actuator 330. The waveguide 322 further comprises a pinching feature or nub feature 323 at the exit point touching the eyelid and over the region between the eyelid close to the exit point of the Meibomian gland tissue near the eyelid margin. The actuator 330 can transmit mechanical energy through the waveguide to the Meibomian glands.

Figure 22:
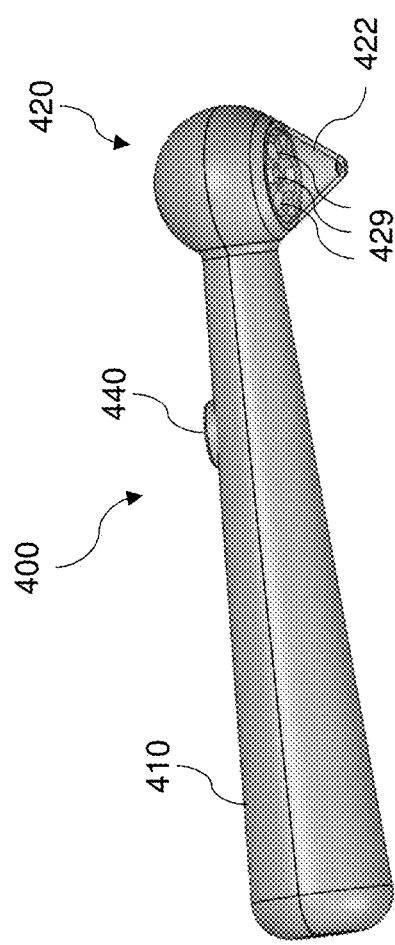
FIG. 22 is a perspective view of a hand-held gland treatment device, according to an embodiment of the present disclosure.

FIG. 22 illustrates another embodiment of a gland treatment device 400. In the illustrated embodiment, the device 400 includes a handle 410, and a head 420 coupled to the distal end of the handle 410. The head 420 comprises a circularly-arranged array of light emitters 429 configured to emit light through a focusing waveguide 422. The waveguide 422 comprises a conical shape, and is configured to direct the light from the emitters to a small area or point. In some embodiments, the device 400 further includes a massaging assembly configured to cause the waveguide to oscillate or vibrate as light is applied to the glands. In some embodiments, the device 400 may be configured to be used by the patient, as opposed to a doctor or clinician. In some embodiments, the device 400 is configured to be operated by a clinician. The device 400 may be controlled to apply the therapy using a button 440. Such a form factor could also be used for the treatment of acne or inflamed pimples with clogged pores that contain blocked sebum oils instead of Meibum oils.

In one embodiment these piezoelectric elements could consist of a flexing bimorph actuator strip known to be low cost and have a frequency excitation range based on geometry from a few 100 Hz to a few kHz. Alternatively, a piezo based vibrating ring bender may be used, such as for example those piezo actuators supplied by Noliac. Owing to the small surface area of this pinched region of the waveguide compared to the much larger surface area of the scleral cover 150, the pressure from the scleral cover 150 to the eyeball is substantially reduced to one that is not concerning and of the same order as normal eyeball rubbing in the range to 0.1-2 psi.

Still other form factors are contemplated by the present disclosure. The form of the device housings described herein may be lightweight and comfortable to a user. In one embodiment, the housing may take the form of goggles strapped to the head of a user. Additionally, the housing element may take the form of an A/R or V/R visor, eyepatch, or mask secured to the head or ears. The device may be fitted at an ophthalmology office in a similar manner to eyeglasses fitting by a trained technician. Additionally, the device housing may take the form of a heating wand that has a diffuse spot with heating tip with a smaller active area typically a few square millimeters in area. This may focus light on either one or two Meibomian glands at any given time. This form of the housing then can be moved slowly back and forward across the eyelid by a user to target each of the Meibomian glands individually and a buzzer to inform the user that the wand can be moved once enough time has passed to provide adequate localized heat. This may be a lower cost housing open form factor which appeals to users but requires additional work on their part to scan across Meibomian glands.

In some embodiments, redundant automatic safety mechanisms are incorporated in the device to ensure the protective scleral cover is being worn by the user during treatment. mechanism for verifying that the protective scleral cover is positioned on the eye can be through through the registration on an RFID chip.

The incorporation of red LEDS or other visible light also on the PCB holding the IR heating LEDs may be of a power that is safe for the eye but is annoying and could also be used as an indication to the user that the protective shield is not in the eye.

A further mechanism for verifying that the protective scleral cover is present is to use a low-cost inspection camera. For example, the same camera used to see Meibum extruded such as an OmniVision OVM6211 can verify the presence or absence of the scleral shield.

Having such a camera system embedded in a handheld may be highly desirable for recording which individual Meibomian glands were targeted in the past and on which eyelid and it is desirable to keep track of which positions were last treated so that all glands received equal amounts of treatment. This camera together with an app can keep track of which eyelid positions were last treated.

Persons skilled in the art will recognize that the devices, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus for optical heating of an eyelid of a patient, comprising:
 a housing configured to be grasped by a human hand;
 at least one light emitter coupled to the housing and configured to emit beams of infrared light for a time period;
 a waveguide component coupled to the at least one emitter and configured to direct the beams of infrared light toward the eyelid; and
 a scleral cover configured to couple to the housing, the scleral cover comprising:
  a curved protective portion configured to be positioned over a portion of a patient's eye and having an inner surface and an outer surface, wherein the outer surface comprises a dielectric material configured to reflect infrared light emanating from the at least one light emitter toward the eyelid and transmit visible light toward at least the cornea of the patient, and wherein the inner surface is configured to face the eye and to contact at least a portion of the sclera while being physically separated from the cornea of the patient by a vaulted air gap configured to protect the cornea of the patient from pressure and heat damage, and wherein the vaulted air gap is sized and shaped to thermally isolate at least the cornea of the patient from the beams of infrared light for the time period the beams are emitted, wherein the vaulted air gap is between 300 and 500 microns at the center of the scleral cover.

2. The apparatus of claim 1, wherein the scleral cover includes a biocompatible acrylic material and a titanium dioxide additive incorporated with the biocompatible acrylic material.

3. The apparatus of claim 1, wherein the scleral cover further comprises a tab configured to engage a mechanical coupling feature of the housing.

4. The apparatus of claim 3, further comprising an imaging component coupled to the housing,
 wherein the scleral cover further comprises a viewing window comprising a transparent body coupled to the tab, the transparent body comprising an angled viewing surface forming an oblique angle with the tab, and
 wherein the imaging component is oriented to obtain images of the eyelid of the patient through the viewing window.

5. The apparatus of claim 4, wherein the imaging component is configured to obtain images of an eyelid margin of the patient through the viewing window during a treatment procedure.

6. The apparatus of claim 1, wherein the waveguide component comprises a low durometer material and is at least partially transparent for the infrared light emitted by the light emitter.

7. The apparatus of claim 1, further comprising an actuator coupled to the waveguide component and configured to cause the waveguide component to move in a longitudinally oscillating manner.

8. The apparatus of claim 1, wherein the scleral cover comprises at least one of a temperature circuit or a device identification circuit.

9. The apparatus of claim 8, wherein the at least one of the temperature circuit or the device identification circuit comprises a radiofrequency identification (RFID) circuit disposed on a surface of the scleral cover, and wherein the apparatus further comprises an RFID transceiver coupled to the housing and configured to:
  provide power to the RFID circuit of the scleral cover; and
  receive at least one of a device identification signal or a temperature measurement signal from the RFID circuit of the scleral cover.

10. The apparatus of claim 1, further comprising a light delivery assembly coupled to the housing comprising the at least one light emitter and the waveguide component, wherein the waveguide component is positioned over the at least one light emitter and within a distal opening of the housing.

11. The apparatus of claim 10, wherein the at least one light emitter comprises one or more light emitting diodes (LEDs).

12. The apparatus of claim 11, wherein the one or more LEDs comprise at least one of:
  one or more short wave infrared (SWIR) LEDs configured to emit light having a spectral range of 1050 nm-1200 nm; or
  one or more infrared LEDs configured to emit light having a center wavelength of approximately 980 nm and a spectral range between 940 nm-1000 nm.

13. The apparatus of claim 1, wherein the vaulted air gap is sized to keep the cornea below 39 degrees Celsius for between 2 and 5 minutes, when the infrared light beam is emitted.

\* \* \* \* \*